(12) United States Patent
Traverso et al.

(10) Patent No.: US 11,684,583 B2
(45) Date of Patent: Jun. 27, 2023

(54) COMPOSITIONS AND RELATED METHODS FOR TARGETED DRUG DELIVERY

(71) Applicants: Massachusetts Institute of Technology, Cambridge, MA (US); The Brigham and Women's Hospital, Inc., Boston, MA (US)

(72) Inventors: Carlo Giovanni Traverso, Newton, MA (US); Ashok Kakkar, Pointe-Claire (CA); Joshua Korzenik, Waban, MA (US); Robert S. Langer, Newton, MA (US); Sufeng Zhang, Cambridge, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 45 days.

(21) Appl. No.: 16/080,737

(22) PCT Filed: Dec. 8, 2017

(86) PCT No.: PCT/US2017/065262
§ 371 (c)(1),
(2) Date: Aug. 29, 2018

(87) PCT Pub. No.: WO2018/106998
PCT Pub. Date: Jun. 14, 2018

(65) Prior Publication Data
US 2020/0352870 A1 Nov. 12, 2020

Related U.S. Application Data

(60) Provisional application No. 62/431,672, filed on Dec. 8, 2016.

(51) Int. Cl.
| | | |
|---|---|---|
| *A61K 9/50* | (2006.01) | |
| *C08F 220/56* | (2006.01) | |
| *A61K 47/34* | (2017.01) | |
| *A61K 9/51* | (2006.01) | |
| *A61K 38/19* | (2006.01) | |
| *A61K 31/58* | (2006.01) | |
| *A61K 47/54* | (2017.01) | |
| *A61K 47/58* | (2017.01) | |
| *A61K 9/00* | (2006.01) | |
| *C08F 220/54* | (2006.01) | |
| *C08F 224/00* | (2006.01) | |

(52) U.S. Cl.
CPC .......... *A61K 9/5052* (2013.01); *A61K 9/0024* (2013.01); *A61K 9/5026* (2013.01); *A61K 9/5036* (2013.01); *A61K 9/5169* (2013.01); *A61K 31/58* (2013.01); *A61K 38/193* (2013.01); *A61K 47/34* (2013.01); *A61K 47/54* (2017.08); *A61K 47/58* (2017.08); *C08F 220/54* (2013.01); *C08F 220/56* (2013.01); *C08F 224/00* (2013.01)

(58) Field of Classification Search
None
See application file for complete search history.

(56) References Cited

U.S. PATENT DOCUMENTS

| | | |
|---|---|---|
| 2010/0168044 A1 | 7/2010 | Misra |
| 2010/0203142 A1 | 8/2010 | Zhang et al. |
| 2011/0097416 A1 | 4/2011 | Nguyen et al. |
| 2012/0231072 A1 | 9/2012 | Kang-Mieler et al. |
| 2013/0280334 A1 | 10/2013 | Karp et al. |
| 2014/0065226 A1 | 3/2014 | Brey et al. |

(Continued)

FOREIGN PATENT DOCUMENTS

| | | |
|---|---|---|
| CN | 107158481 A | 9/2017 |
| WO | WO 96/20698 A2 | 7/1996 |
| WO | WO 2012/040623 A2 | 3/2012 |

(Continued)

OTHER PUBLICATIONS

Constantin et al., "Poly(N-isopropylacrylamide-co-methacrylic acid) pH/thermo-responsive porous hydrogels as self-regulated drug delivery system", European Journal of Pharmaceutical Science, 2014, 62, pp. 86-95. (Year: 2014).*
Shen et al., "Preparation and characterization of thermo-responsive albumin nanospheres", International Journal of Pharmaceutics, 2008, 346, pp. 133-142. (Year: 2008).*
Martin et al., "Surface Functionalization of Nanomaterials with Dendritic Groups: Toward Enhanced Binding to Biological Targets", J. Am. Chem. Soc. 2009, 131, 2, pp. 734-741. (Year: 2009).*

(Continued)

*Primary Examiner* — Melissa L Fisher
(74) *Attorney, Agent, or Firm* — Wolf, Greenfield & Sacks, P.C.

(57) ABSTRACT

Compositions, articles, and methods for targeted drug delivery, such as thermoresponsive hydrogel polymers, are generally provided. In one aspect, the compositions and articles comprise a thermoresponsive hydrogel polymer comprising a releasable therapeutic agent. In some cases, the compositions described herein have advantageous combinations of properties including mechanical strength, biocompatibility, tunable charge densities, thermal responsiveness, drug loading, and/or configurations for targeted drug delivery. In one embodiment, the composition comprises a solution comprising a thermoresponsive polymer including one or more ligands attached to the polymer, wherein the solution is configured to undergo a sol-to-gel transition under physiological conditions. In another embodiment, the composition comprises a plurality of nanoparticles e.g., associated with the thermoresponsive polymer. In yet another embodiment, the composition comprises a therapeutic agent e.g., associated with the nanoparticles and/or thermoresponsive polymer.

17 Claims, 15 Drawing Sheets

(56) References Cited

U.S. PATENT DOCUMENTS

2015/0147270 A1      5/2015   Merlin et al.

FOREIGN PATENT DOCUMENTS

| WO | WO 2012/040623 A3 | 3/2012 |
| WO | WO 2012/123275 A1 | 9/2012 |

OTHER PUBLICATIONS

Socha et al., "Stealth nanoparticles coated with heparin as peptide or protein carriers", Journal of Drug Targeting, 2009, 17(8), pp. 575-585. (Year: 2009).*

Actis et al., Inflammatory bowel diseases: Current problems and future tasks. World J Gastrointest Pharmacol Ther. Aug. 6, 2014;5(3):169-74. doi: 10.4292/wjgpt.v5.i3.169.

Canny et al., Lipid mediator-induced expression of bactericidal/permeability-increasing protein (BPI) in human mucosal epithelia. Proc Natl Acad Sci U S A. Mar. 19, 2002;99(6):3902-7. Epub Mar. 12, 2002.

Carlmark et al., Dendritic architectures based on bis-MPA: functional polymeric scaffolds for application-driven research. Chem Soc Rev. Jul. 7, 2013;42(13):5858-79. doi: 10.1039/c3cs60101c. Epub Apr. 30, 2013.

Danese et al., Ulcerative colitis. N Engl J Med. Nov. 3, 2011;365(18):1713-25. doi: 10.1056/NEJMra1102942.

De Souza et al., Immunopathogenesis of IBD: current state of the art. Nat Rev Gastroenterol Hepatol. Jan. 2016;13(1):13-27. doi: 10.1038/nrgastro.2015.186. Epub Dec. 2, 2015.

Dou et al., Biodegradable thermogelling polymers: Working towards clinical applications. Adv Healthc Mater. Jul. 2014;3(7):977-88. doi: 10.1002/adhm.201300627. Epub Feb. 1, 2014.

Ediger et al., Predictors of medication adherence in inflammatory bowel disease. Am J Gastroenterol. Jul. 2007; 102(7):1417-26. Epub Apr. 16, 2007.

Greenberg, Topically Active Corticosteroids for Colitis. Ch. 15 in Advanced Therapy of Inflammatory Bowel Disease. Ed by Bayless et al., London:BC Decker Inc., 2001. pp. 73-76.

Jain et al., Target-specific drug release to the colon. Expert Opin Drug Deliv. May 2008;5(5):483-98. doi: 10.1517/17425247.5.5.483. Epub May 20, 2008.

Kornbluth et al., Practice Parameters Committee of the American College of Gastroenterology. Ulcerative colitis practice guidelines in adults: American College Of Gastroenterology, Practice Parameters Committee. Am J Gastroenterol. Mar. 2010;105(3):501-23; quiz 524. doi: 10.1038/ajg.2009.727. Epub Jan. 12, 2010.

Lamprecht et al., Biodegradable nanoparticles for targeted drug delivery in treatment of inflammatory bowel disease. J Pharmacol Exp Ther. Nov. 2001;299(2):775-81.

Mattar et al., Current management of inflammatory bowel disease and colorectal cancer. Gastrointest Cancer Res. Mar./Apr. 2011;4(2):53-61.

Matzen, Budesonide enema in distal ulcerative colitis. A randomized dose-response trial with prednisolone enema as positive control. The Danish Budesonide Study Group. Scand J Gastroenterol. Dec. 1991;26(12):1225-30.

Monajemi et al., Inflammatory bowel disease is associated with increased mucosal levels of bactericidal/permeability-increasing protein. Gastroenterology. Mar. 1996;110(3):733-9.

Nyman-Pantelidis et al., Pharmacokinetics and retrograde colonic spread of budesonide enemas in patients with distal ulcerative colitis. Aliment Pharmacol Ther. Dec. 1994;8(6):617-22.

Ramasundara et al., Defensins and inflammation: the role of defensins in inflammatory bowel disease. J Gastroenterol Hepatol. Feb. 2009;24(2):202-8. doi: 10.1111/j.1440-1746.2008.05772.x.

Roldo et al., Azo compounds in colon-specific drug delivery. Expert Opin Drug Deliv. Sep. 2007;4(5):547-60. Epub Sep. 20, 2007.

Sakhalkar et al., Enhanced adhesion of ligand-conjugated biodegradable particles to colitic venules. FASEB J. May 2005;19(7):792-4. Epub Mar. 11, 2005.

Sakhalkar et al., Leukocyte-inspired biodegradable particles that selectively and avidly adhere to inflamed endothelium in vitro and in vivo. Proc Natl Acad Sci USA. Dec. 22, 2003; 100(26):15895-900. Epub Dec. 10, 2003.

Sinha et al., A thermo-sensitive delivery platform for topical administration of inflammatory bowel disease therapies. Gastroenterology. Jul. 2015;149(1):52-5. Suppl Mater., 2 pages.

Tirosh et al., Transferrin as a luminal target for negatively charged liposomes in the inflamed colonic mucosa. Mol Pharm. Jul.-Aug. 2009;6(4):1083-91. doi: 10.1021/mp9000926. Epub Jun. 26, 2006.

Wang et al., Human serum albumin (HSA) nanoparticles stabilized with intermolecular disulfide bonds. ChemCommun (Camb). Mar. 18, 2013;49(22):2234-6. doi: 10.1039/c3cc38397k. Epub Jan. 30, 2013. Supp Info, pp. S1-S16.

Wilson et al., Orally delivered thioketal nanoparticles loaded with TNF-$\alpha$-siRNA target inflammation and inhibit gene expression in the intestines. Nat Mater. Nov. 2010;9(11):923-8. doi: 10.1038/nmat2859. Epub Oct. 10, 2010.

Zhang et al., An inflammation-targeting hydrogel for local drug delivery in inflammatory bowel disease. Sci Transl Med. Aug. 12, 2015;7(300):300ra128(1-10). doi: 10.1126/scitranslmed.aaa5657.

Zhang et al., Drug delivery targeting inflammation in ulcerative colitis. Poster Presentation at The Crohn's & Colitis Foundation of America's Clinical & Research Conference: Advances in Inflammatory Bowel Diseases (AIBD) Conference, Dec. 8-10, 2016, Orlando, FL, USA.

Zhang et al., Abstract of Drug delivery targeting inflammation in ulcerative colitis. Poster Presentation at The Crohn's & Colitis Foundation of America's Clinical & Research Conference: Advances in Inflammatory Bowel Diseases (AIBD) Conference, Dec. 8-10, 2016, Orlando, FL, USA. Published in Inflammatory Bowel Diseases, vol. 23(Suppl 1):S83:Feb. 2017. 1 page.

International Preliminary Report on Patentability dated Jun. 20, 2019 for Application No. PCT/US2017/065262.

PCT/US2017/065262, Mar. 5, 2018, International Search Report and Written Opinion.

International Search Report and Written Opinion dated Mar. 5, 2018 for Application No. PCT/US2017/06526.

Arnaud, Structure of folic acid bound to folate receptor is solved. Chem Eng News. Jul. 22, 2013;91(29):1-4. Epub Jul. 18, 2013.

Soppimath et al., Multifunctional core/shell nanoparticles self-assembled from pH-induced thermosensitive polymers for targeted intracellular anticancer drug delivery. Adv Funct Mater. Jan. 9, 2007;17(3):355-62.

Zhang et al., Magnetic drug-targeting carrier encapsulated with thermosensitive smart polymer: Core-shell nanoparticle carrier and drug release response. Acta Biomater. Jun. 29, 2007;3(6):838-50.

* cited by examiner

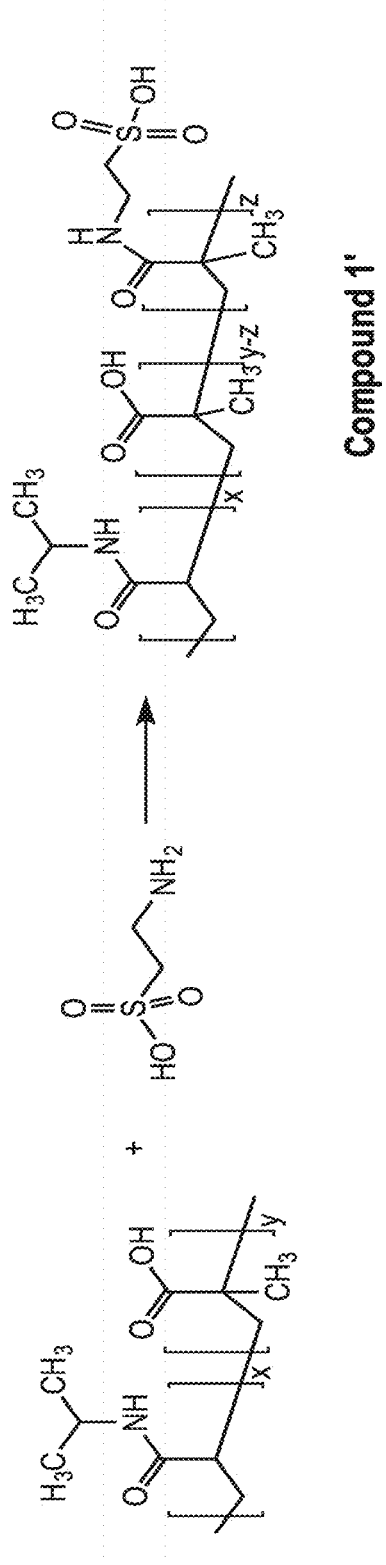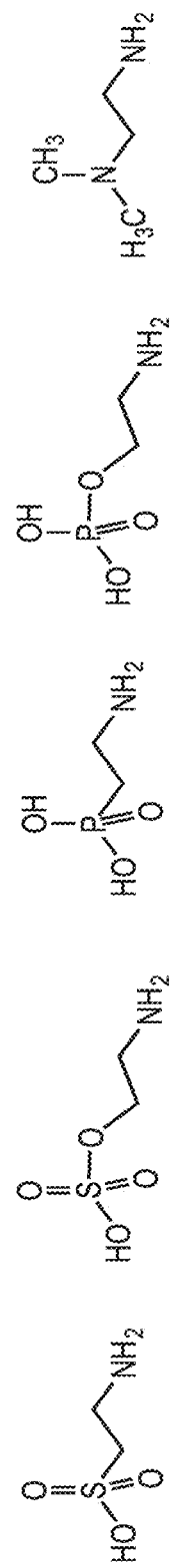
FIG. 2A

Compound 8

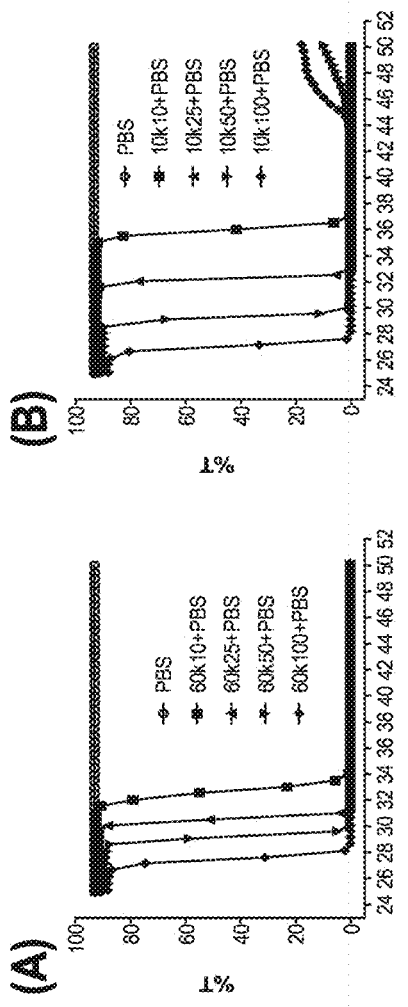

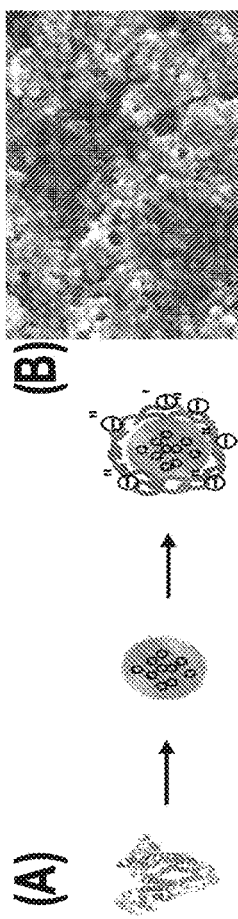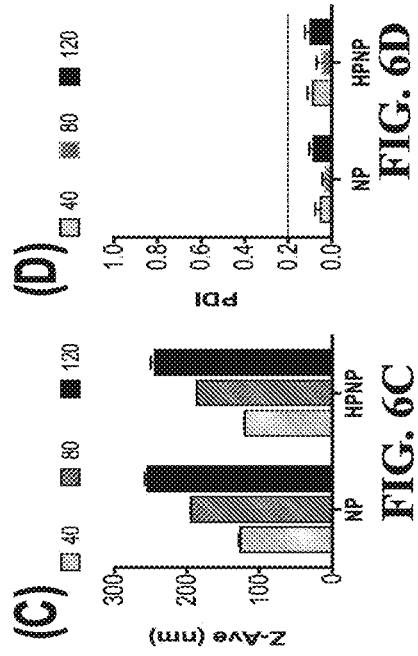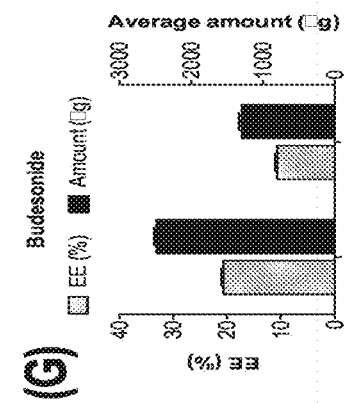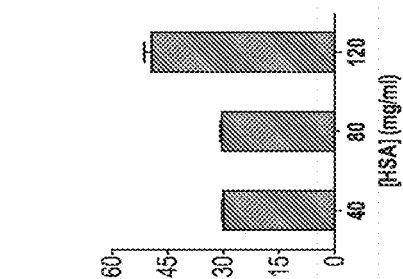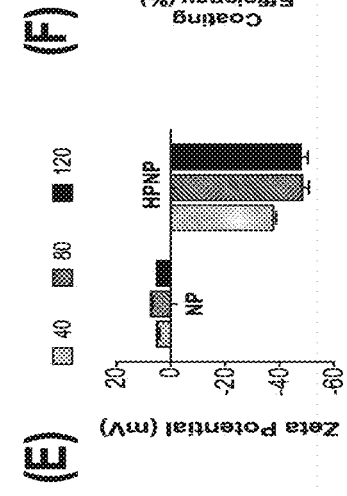
FIG. 6A FIG. 6B FIG. 6C FIG. 6D
FIG. 6E FIG. 6F FIG. 6G FIG. 6H

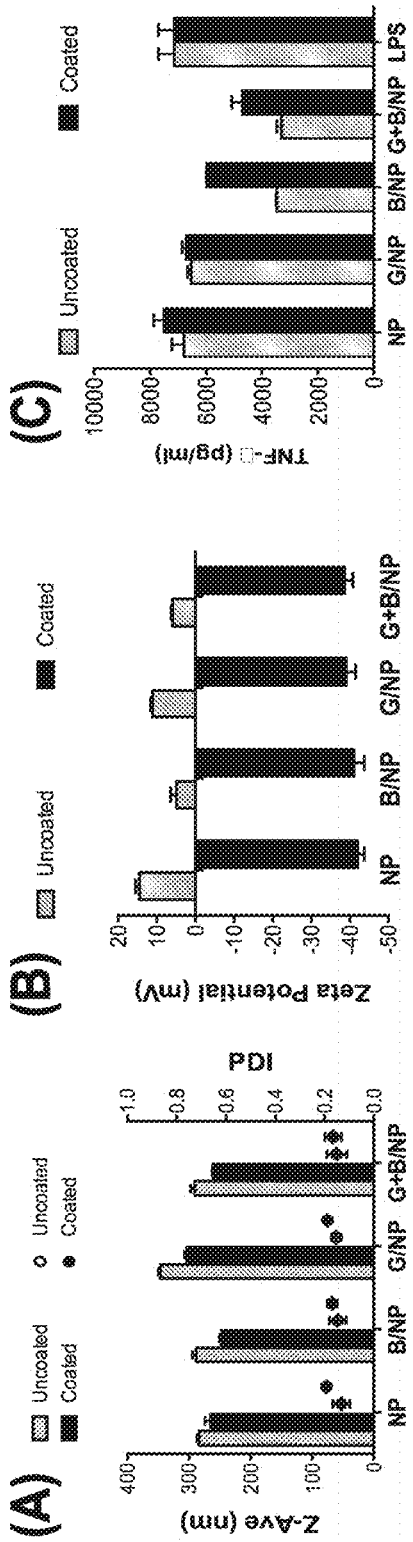
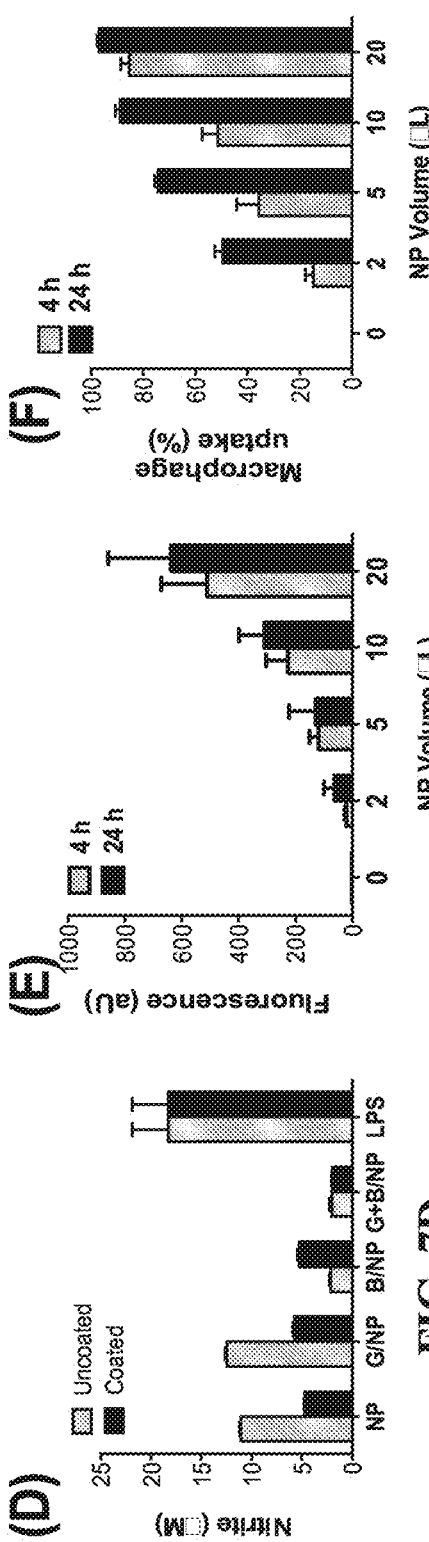

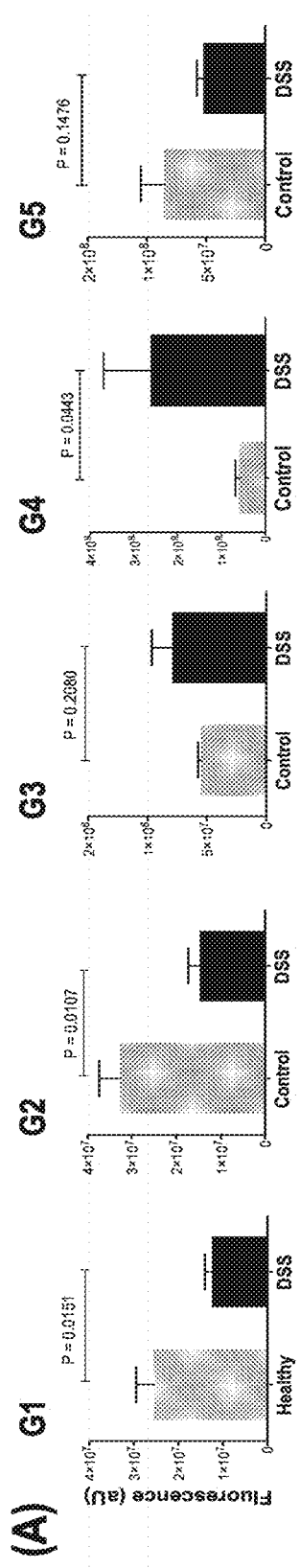
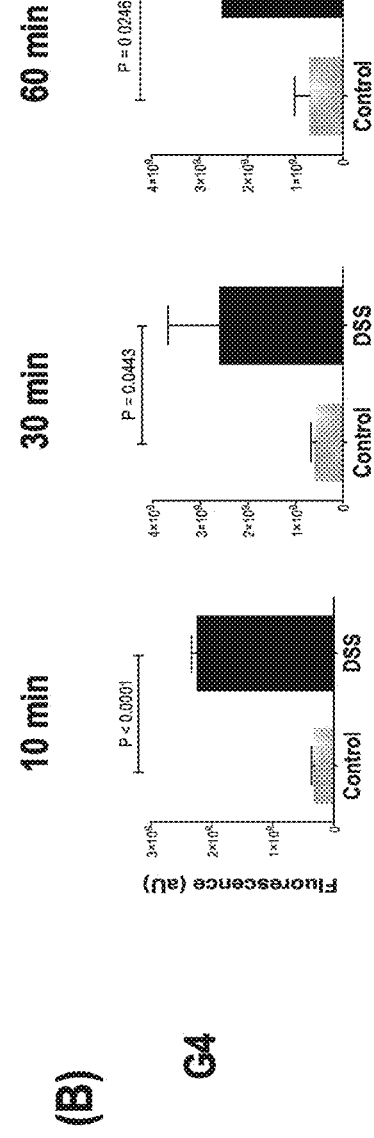
FIG. 8A
FIG. 8B

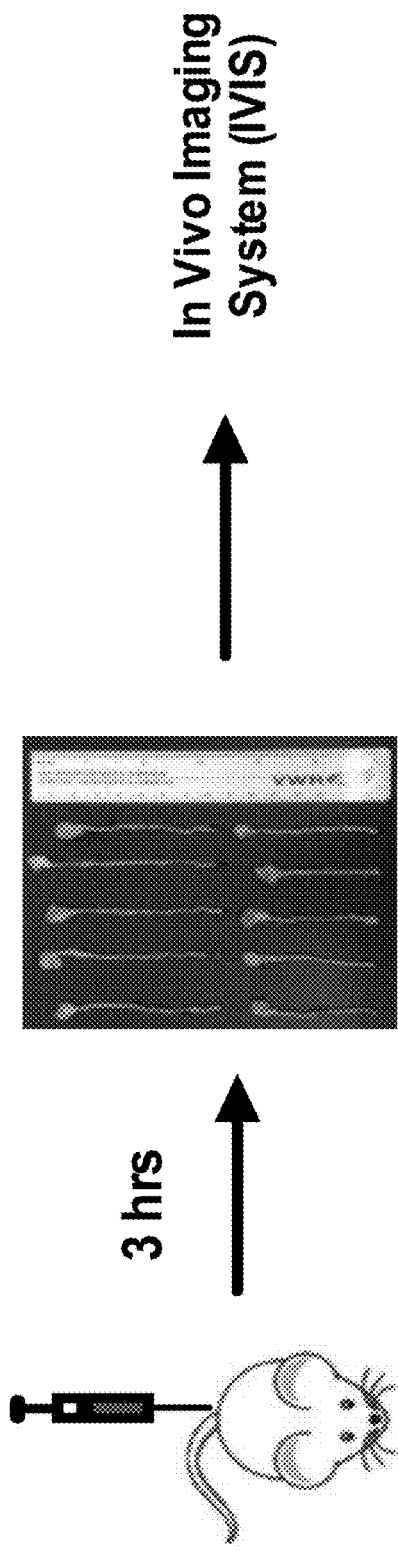
FIG. 9A
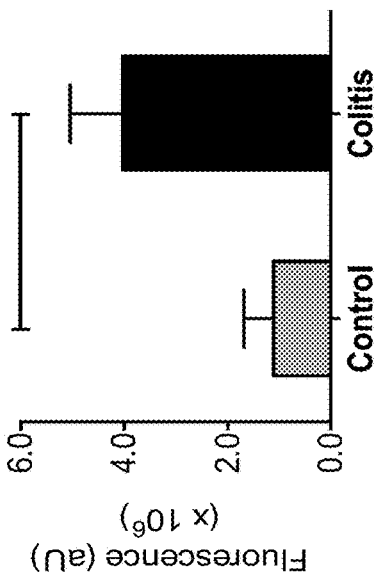
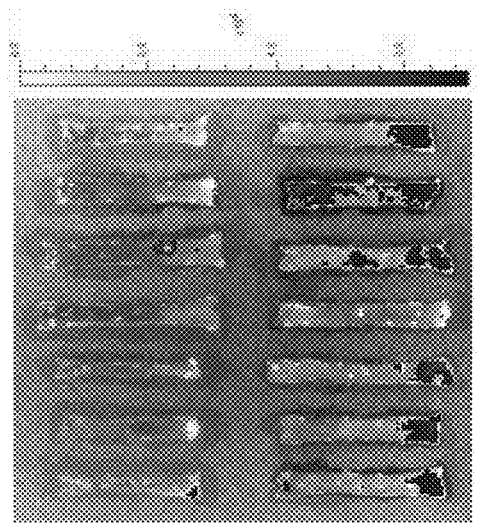
FIG. 9B

COMPOSITIONS AND RELATED METHODS FOR TARGETED DRUG DELIVERY

RELATED APPLICATIONS

This application is a national stage filing under 35 U.S.C. 371 of International Patent Application Serial No. PCT/US2017/065262, filed Dec. 8, 2017, entitled "COMPOSITIONS AND RELATED METHODS FOR TARGETED DRUG DELIVERY", which claims priority under 35 U.S.C. § 119(e) to co-pending U.S. Provisional Application Ser. No. 62/431,672 filed Dec. 8, 2016, each of which is incorporated herein by reference in its entirety for all purposes.

FEDERALLY SPONSORED RESEARCH

This invention was made with Government support under Grant No. R37-EB000244 awarded by the National Institutes of Health. The Government has certain rights in the invention.

FIELD OF THE INVENTION

This invention generally relates to compositions and related methods for targeted drug delivery including, for example, thermoresponsive hydrogels.

BACKGROUND OF THE INVENTION

Ulcerative Colitis (UC), one of the two main variants of Inflammatory Bowel Disease (IBD), is generally characterized by chronic inflammation in the colon extending from the rectum to potentially involve the entire colon. Current state-of-the-art drug delivery systems for IBD treatment are typically based on normal gastroenterology, such as pH-, time-, and pressure-triggered systems to control drug release in the entire colon. However, these approaches generally release drugs to the entire colon instead of the site of inflammation in the inflamed colonic mucosa. Accordingly, improved methods, systems, and compositions are needed.

SUMMARY OF THE INVENTION

The present invention generally relates to compositions and related methods for targeted drug delivery.

In one aspect, articles are provided. In some embodiments, the article comprises a solution comprising a plurality of nanoparticles and a thermoresponsive polymer comprising one or more ligands attached to the polymer, wherein the solution is configured to undergo a sol-to-gel transition between ambient conditions and physiological conditions, the plurality of nanoparticles comprises a therapeutic agent and the one or more ligands comprise a negatively charged functional group under physiological conditions.

In some embodiments, the article comprises a thermoresponsive polymer comprising a polymer backbone, a plurality of nanoparticles associated with the polymer, the plurality of nanoparticles comprising one or more therapeutic agents, and a ligand attached to the polymer, the ligand configured to adhere to an inflamed tissue of a subject, wherein the thermoresponsive polymer has a lower critical solution temperature of greater than or equal to 32° C. and less than or equal to 42° C.

In some embodiments, the article comprises a thermoresponsive polymer comprising a polymer backbone, a plurality of nanoparticles associated with the polymer, the plurality of nanoparticles comprising one or more therapeutic agents, and a ligand attached to the polymer comprising a negatively charged functional group under physiological conditions, wherein the thermoresponsive polymer comprises acrylamide, methylacrylamide, vinylcaprolactam, or derivatives thereof.

In some embodiments, the article comprises a plurality of nanoparticles comprising a shell and/or a matrix, a coating disposed on a surface of the nanoparticle, and a therapeutic agent encapsulated or embedded within the nanoparticle, wherein the shell and/or the matrix comprises albumin and wherein the coating comprises heparin.

In another aspect, methods for administering a therapeutic agent are provided. In some embodiments, the method comprises providing a solution comprising a thermoresponsive polymer and an therapeutic agent to a location internal to a subject, such that upon reaching a physiological temperature at the location internal to the subject, the solution forms a hydrogel and the hydrogel adheres to the location internal to the subject, and releasing the therapeutic agent at the location internal to the subject, wherein the hydrogel network comprises one or more ligands having a negatively charged functional group under physiological conditions.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2A is a chemical reaction scheme for forming an exemplary thermoresponsive composition, according to one set of embodiments;

FIG. 3A is a plot of percent transmittance versus temperature for 60 k PNIPAM-MAA in PBS at a concentration of 10, 25, 50 and 100 mg/ml, according to one set of embodiments;

FIG. 3B is a plot of percent transmittance versus temperature for 60 k PNIPAM-MAA in PBS at a concentration of 10, 25, 50 and 100 mg/ml, according to one set of embodiments;

FIG. 3C is a plot of lower critical solution temperature (LCST) for 60 k and 10 k PNIPAM-MAA, according to one set of embodiments;

FIG. 3D is a plot of percent transmittance versus temperature for 60 k PNIPAM-MAA at a concentration of 10 mg/ml with 10 k dextran at various concentrations, according to one set of embodiments;

FIG. 3E is a plot of percent transmittance versus temperature for 60 k PNIPAM-MAA at a concentration of 10 mg/ml with 70 k dextran at various concentrations, according to one set of embodiments;

FIG. 3F is a plot of LCST for 60 k and 10 k PNIPAM-MAA with 10 k or 70 k dextran, according to one set of embodiments;

FIG. 6A is a schematic illustration of an exemplary nanoparticle comprising human serum albumin (HSA), according to one set of embodiments;

FIG. 6B is a scanning electron microscopy (SEM) image of exemplary nanoparticles, according to one set of embodiments;

FIG. 6C is a plot of average zeta (nm) for uncoated (NP) and heparin coated (HPNP) nanoparticles, according to one set of embodiments;

FIG. 6D is a plot of polydispersity index (PDI) for uncoated (NP) and heparin coated (HPNP) nanoparticles, according to one set of embodiments;

FIG. 6E is a plot of zeta potential (mV) for uncoated (NP) and heparin coated (HPNP) nanoparticles, according to one set of embodiments;

FIG. 6F is a plot of coating efficiency of heparin on nanoparticles at various concentrations of HSA, according to one set of embodiments;

FIG. 6G is a plot of percent encapsulation efficiency and drug amount for budesonide loaded nanoparticles, according to one set of embodiments;

FIG. 6H is a plot of percent encapsulation efficiency and drug amount for granulocyte macrophage-co stimulating factor (GM-CSF) loaded nanoparticles, according to one set of embodiments;

FIG. 7A is a plot of average zeta (nm) and PDI for unloaded (NP), budesonide loaded (B/NP), GM-CSF loaded (G/NP), and budesonide and GM-CSF loaded (G+B/NP) nanoparticles, according to one set of embodiments;

FIG. 7B is a plot of zeta potential (mV) for unloaded (NP), budesonide loaded (B/NP), GM-CSF loaded (G/NP), and budesonide and GM-CSF loaded (G+B/NP) nanoparticles, according to one set of embodiments;

FIG. 7C is a plot of inhibition on TNF-alpha secretion in macrophage culture by unloaded (NP), budesonide loaded (B/NP), GM-CSF loaded (G/NP), and budesonide and GM-CSF loaded (G+B/NP) nanoparticles, according to one set of embodiments;

FIG. 7D is a plot of inhibition of nitric oxide production in macrophage culture unloaded (NP), budesonide loaded (B/NP), GM-CSF loaded (G/NP), and budesonide and GM-CSF loaded (G+B/NP) nanoparticles, according to one set of embodiments;

FIG. 7E is a plot of macrophage uptake of HSA coated nanoparticles as determined by fluorescence microscopy versus nanoparticle volume, according to one set of embodiments;

FIG. 7F is a plot of macrophage uptake of HSA coated nanoparticles as determined by flow cytometry versus nanoparticle volume, according to one set of embodiments;

FIG. 8A is a plot of NP retention determined by fluorescence intensity for dissected colons of control mice or mice with colitis (DSS) administered with nanoparticles of various size and zeta potential (G1, G2, G3, G4, and G5), according to one set of embodiments;

FIG. 8B is a plot of NP retention determined by fluorescence intensity for dissected colons of control mice or mice with colitis (DSS) administered with nanoparticles at various time points, according to one set of embodiments;

FIG. 9A is a schematic illustration of an exemplary method for quantifying the retention of nanoparticles administered to control or colitis mice colons, according to one set of embodiments;

FIG. 9B is an exemplary quantification and related plot of retention determined by fluorescence intensity for an exemplary group of budesonide-loaded HSA NPs administered to control and colitis mice colons, according to one set of embodiments;

DETAILED DESCRIPTION OF THE INVENTION

Figure 1:
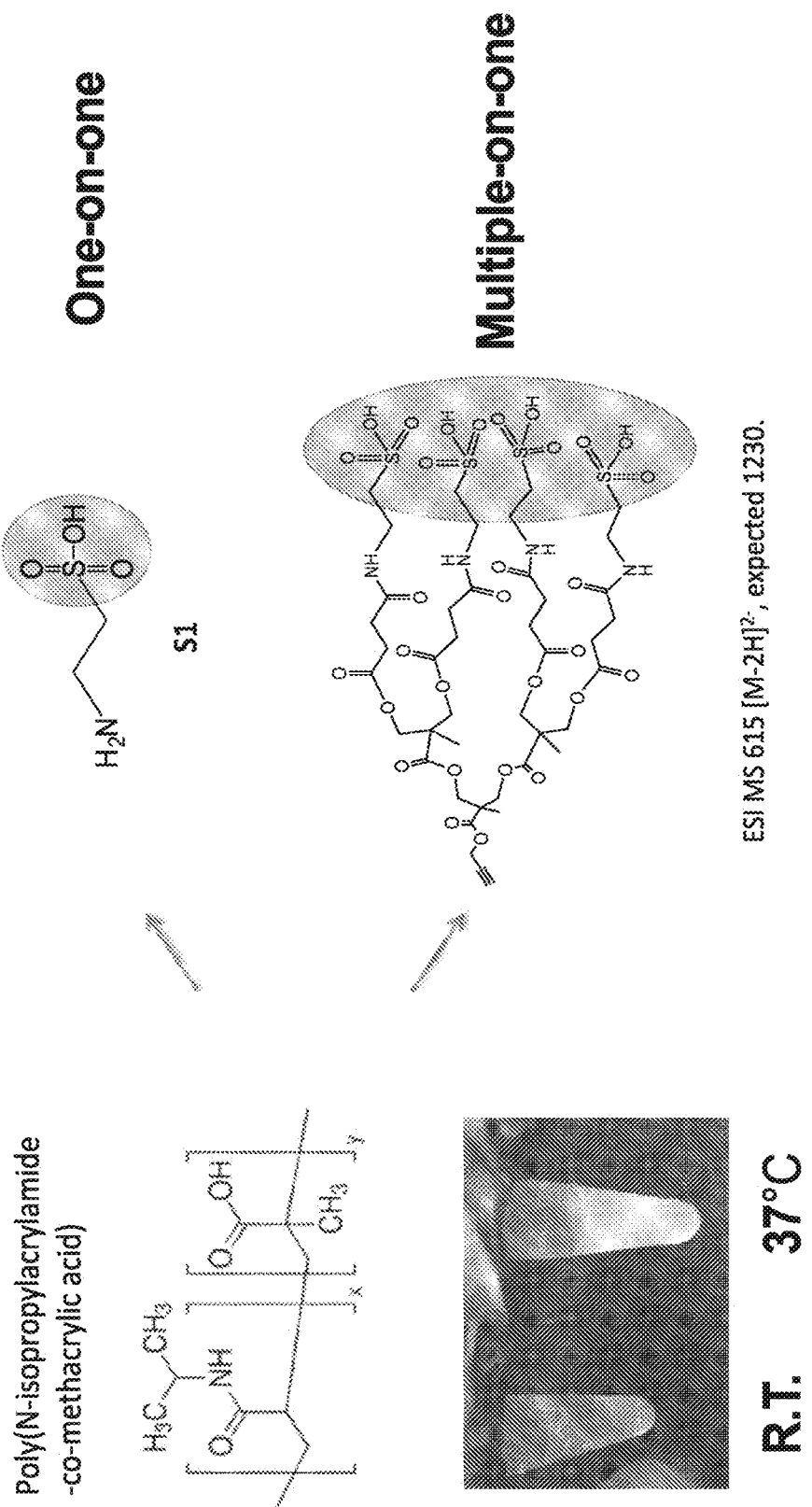
FIG. 1 is a schematic illustration of compositions for targeted drug delivery, according to one set of embodiments.

Compositions, articles, and methods for targeted drug delivery, such as thermoresponsive hydrogel polymers, are generally provided. In one aspect, the compositions and articles comprise a thermoresponsive hydrogel polymer comprising one or more releasable therapeutic agents. In some cases, the compositions described herein have advantageous combinations of properties including mechanical strength, biocompatibility, tunable charge densities, thermal responsiveness, drug loading. and/or configurations for targeted drug delivery. In one embodiment, the composition comprises a solution comprising a thermoresponsive polymer including one or more ligands attached to the polymer, wherein the solution is configured to undergo a sol-to-gel transition between ambient conditions (e.g., room temperature and atmospheric pressure) under physiological conditions (e.g., at or about 37° C.). For example, in some embodiments, the thermoresponsive polymer is a hydrogel (e.g., at a temperature greater than the LCST of the thermoresponsive polymer). In another embodiment, the composition comprises a plurality of nanoparticles e.g., associated with the thermoresponsive polymer. In yet another embodiment, the composition comprises one or more therapeutic agents e.g., associated with the nanoparticles and/or thermoresponsive polymer.

It has been discovered that the compositions described herein advantageously can provide targeted delivery of one or more therapeutic agents at a particular location internal to a subject. In some embodiments, the location internal to the subject is characterized by local and/or regional inflammation. In an exemplary set of embodiments, the composition is configured to selectively adhere to a surface of inflamed tissue in a subject (e.g., ulcers, inflamed mucosal tissue, etc.). In some embodiments, the composition is formed by the reaction of a thermoresponsive polymer with one or more ligands. In certain embodiments, the ligand comprises one or more functional groups capable of selectively adhering (e.g., bonding) with a surface of inflamed tissue. For example, in some embodiments, the ligand comprises a functional group comprising sulfonic acid, phosphonic acid, sulfates, phosphates, or derivatives thereof. Esters and/or salts of the functional groups are also possible. In some cases, the polymer comprising the ligand may be mono- or poly-functional. For example, a dendrimer comprising the ligand may be reacted with a thermoresponsive polymer to form the composition.

The compositions described herein may offer several advantages over traditional materials (e.g., for drug delivery and/or biological applications) including formation of a hydrogel under physiological conditions, selected adhesion and/or targeted drug delivery to a site of inflammation in a subject, sustained drug release (e.g., for at least 10 minutes) at a desired location internal to a subject, reduced or eliminated exposure of healthy or distant tissue to a selected therapeutic agent, and/or obtaining an aqueous phase at room temperature. Additionally, the hydrogels described herein are generally formed in the presence of physiological conditions (e.g., at or around 37° C., in physiologic fluids such as gastric fluid) and/or may be relatively easily removed from the subject at a desired time. In some embodiments, the compositions described herein may advantageously maintain adhered to a location internal to a subject with low to no potential for gastric or intestinal obstruction and/or perforation.

The compositions and articles described herein may be retained internally of the subject at a surface of locations such as the stomach, the bladder, the esophagus, the colon, or the like. In certain embodiments, the location internal to the subject is one or more surfaces of the colon, the duodenum, the ileum, the jejunum, the stomach, or the esophagus. In a particular embodiments, the article is designed for gastric retention. In some embodiments, the composition (e.g., thermoresponsive polymer or solution thereof) may be administered orally, rectally, vaginally, nasally, uretherally, endoscopically, or cytoscopically. In certain embodiments, upon reaching a location internal to the subject (e.g., the gastrointestinal tract), at least a portion of the composition adheres to a surface of the location internal to the subject. In some cases, upon adhering to the surface of the location internal to the subject, a therapeutic agent associated with the composition is released at the location internal to the subject. In certain embodiments, the location internal to the subject is a site of inflammation in the colon, the duodenum, the ileum, the jejunum, the stomach, or the esophagus. As described above and herein, in some embodiments, a therapeutic agent may be released during and/or after adhering of the composition to (inflamed) tissue located internal to the subject.

The thermoresponsive polymers described herein may be useful in a number of applications including, for example, gastric retention. In some embodiments, the thermoresponsive polymer is a solution until, under physiological conditions, the thermoresponsive polymer undergoes a sol-to-gel transition and obtain a hydrogel state.

In some embodiments, the thermoresponsive polymer composition comprises a polymer network such as a hydrogel. In some embodiments, the thermoresponsive polymer is a copolymer comprising a first monomer and a second monomer. For example, in some embodiments, the thermoresponsive polymer is formed by the reaction of the first monomer and the second monomer such that the thermoresponsive polymer comprises repeat units of the first monomer and second monomer.

In some embodiments, the first monomer comprises acrylamide, methylacrylamide, vinylcaprolactam, or derivatives thereof. Non-limiting examples of suitable first monomers include, but are not limited to, N-isopropyl acrylamide (NIPAM), N-isopropyl methacrylamide (NIPMAM), N,N-diethyl-acrylamide (DEAAAM), N-vinylcaprolactam (VCL), 3-(N,N-dimethylamino) propylmethacrylamide (DMAPMA), and derivatives thereof. Those of ordinary skill in the art would be capable of selecting additional suitable monomers for forming a thermoresponsive polymer based upon the teachings described herein.

In certain embodiments, the second monomer comprises a terminal carboxylic acid. For example, in certain embodiments, the second monomer comprises alkyl acrylic acid or derivatives thereof (e.g., acrylic acid, methacrylic acid).

Those of ordinary skill in the art would be capable of selecting additional suitable monomers for forming a thermoresponsive polymer based upon the teachings described herein. For example, in some embodiments, the first and second monomer may be selected such that the thermoresponsive polymer formed by the first and second monomer has a lower critical solution temperature (LCST) of greater than or equal to 32° C. and less than or equal to 42° C., such that the thermoresponsive polymer forms a hydrogel under physiological conditions.

In some embodiments, the thermoresponsive polymer comprises a structure as in formula (I):

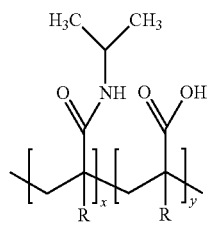

where x is 0-1, y is 1-x, and each R is the same or different and is hydrogen or alkyl. In some embodiments, each R is the same or different and is hydrogen or methyl.

FIG. 1 shows an exemplary thermoresponsive polymer, according to some embodiments. For example, in some embodiments, the thermoresponsive polymer is poly(N-isopropylacrylamide-co-methacrylic acid). In an exemplary embodiment, the thermoresponsive polymer is poly(N-isopropylacrylamide-co-acrylic acid). In another exemplary embodiment, the thermoresponsive polymer is poly(N-isopropylmethacrylamide-co-methacrylic acid). In yet another exemplary embodiment, the thermoresponsive polymer is poly(N-isopropylmethacrylamide-co-acrylic acid). Other thermoresponsive polymers are also possible.

In certain embodiments, the ratio of the first monomer to the second monomer present in the thermoresponsive polymer is at least about 1:5, at least about 1:4, at least about 1:3, at least about 1:2, or at least about 1:1, at least about 2:1, at least about 3:1, or at least about 4:1. In certain embodiments, the ratio of the first monomer to the second monomer present in the thermoresponsive polymer is less than or equal to about 5:1, less than or equal to about 4:1, less than or equal to about 3:1, less than or equal to about 2:1, less than or equal to about 1:1, less than or equal to about 1:2, less than or equal to about 1:3, or less than or equal to about 1:4. Combinations of the above referenced ranges are also possible (e.g., between 1:5 and 5:1, between 1:1 and 4:1, between 2:1 and 4:1). In an exemplary embodiment, the ratio of the first monomer to the second monomer is 1:1. That is to say, in some such embodiments, the thermoresponsive polymer has a structure as in formula (I) where x is 0.5 and y is 0.5. Other values for x and y are also possible.

In some embodiments, x is greater than or equal to 0.01, greater than or equal to 0.05, greater than or equal to 0.1, greater than or equal to 0.2, greater than or equal to 0.3, greater than or equal to 0.4 greater than or equal to 0.5, greater than or equal to 0.6, greater than or equal to 0.7, greater than or equal to 0.8, greater than or equal to 0.9, or greater than or equal to 0.95. In certain embodiments, x is less than or equal to 0.99, less than or equal to 0.95, less than or equal to 0.9, less than or equal to 0.8, less than or equal to 0.7, less than or equal to 0.6, less than or equal to 0.5, less than or equal to 0.4, less than or equal to 0.3, less than or equal to 0.2, less than or equal to 0.1, or less than or equal to 0.05. Combinations of the above-referenced ranges are possible (e.g., greater than or equal to 0.01 and less than or equal to 0.99, greater than or equal to 0.3 and less than or equal to 0.7). Other ranges and combinations are also possible.

In some embodiments, the thermoresponsive polymer may comprise one or more functional groups such that the thermoresponsive polymer may (selectively) adheres to a surface of inflamed tissue. In certain embodiments, the thermoresponsive polymer adheres to a surface of inflamed tissue but does not adhere (e.g., may be removed from the tissue with order(s) of magnitude lower force from the tissue as compared to when the thermoresponsive polymer adheres) to a surface of otherwise healthy tissue. In an exemplary set of embodiments, the thermoresponsive polymer may comprise one or more negatively charged functional groups (e.g., under physiological conditions).

In certain embodiments, the thermoresponsive polymer (and/or the functional groups thereon) may adhere to inflamed tissue via the formation of a bond, such as an ionic bond, a covalent bond, a hydrogen bond, Van der Waals (e.g., electrostatic) interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups. The bond may also be, for example, between sulfonic acid and a positively charged functional group or phosphonic acid and a positively charged functional group (e.g., present on the surface of the location internal to the subject). Other bonds are also possible.

In some embodiments, the second monomer may be (further) reacted with one or more ligands to form the thermoresponsive polymer (e.g., the thermoresponsive polymer comprising one or more functional groups). In some embodiments, the ligand comprises a negatively charged functional group (e.g., under physiological conditions). In certain embodiments, the ligand comprises comprising sulfonic acid, sulfinic acid, phosphonic acid, phsophinic acid, or derivatives thereof. In some embodiments, the ligand may be amine terminated such that the ligand comprising a functional group may react with another functional group (e.g., carboxylic acid) on the second monomer. Non-limiting examples of suitable ligands include N,N-dimethylethylenediamine, taurine, 2-aminoethyl hydrogen sulfate, O-phosphorylethanolamine, and 2-aminoethyl-phosphonic acid, and are shown in FIG. 2A (e.g., Compound 1, Compound 2, Compound 3, Compound 4, and Compound 5).

Those of ordinary skill in the art would be capable of selecting additional suitable ligands based upon the teachings of this specification.

In some embodiments, the thermoresponsive polymer has a structure as in formula (II):

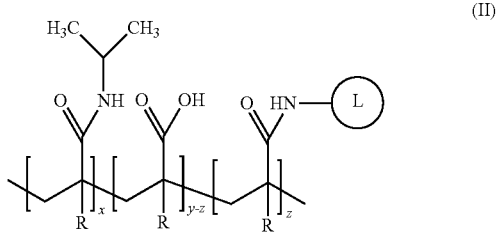

where x is 0-1, y is 1-x, z is 0-1, L is a ligand (e.g., monofunctional ligand, polyfunctional ligand), and each R is the same or different and is hydrogen or alkyl. In some embodiments, each R is the same or different and is hydrogen or methyl.

In some embodiments, z is greater than or equal to 0.01, greater than or equal to 0.05, greater than or equal to 0.1, greater than or equal to 0.2, greater than or equal to 0.3, greater than or equal to 0.4 greater than or equal to 0.5, greater than or equal to 0.6, greater than or equal to 0.7, greater than or equal to 0.8, greater than or equal to 0.9, or greater than or equal to 0.95. In certain embodiments, z is less than or equal to 0.99, less than or equal to 0.95, less than or equal to 0.9, less than or equal to 0.8, less than or equal to 0.7, less than or equal to 0.6, less than or equal to 0.5, less than or equal to 0.4, less than or equal to 0.3, less than or equal to 0.2, less than or equal to 0.1, or less than or equal to 0.05. Combinations of the above-referenced ranges are possible (e.g., greater than or equal to 0.01 and less than or equal to 0.99, greater than or equal to 0.3 and less than or equal to 0.7). Other ranges and combinations are also possible.

In some embodiments, the thermoresponsive polymer may have a particular number average molecular weight. In some embodiments, the number average molecular weight of the thermoresponsive polymer is greater than or equal to 1 kDa and less than or equal to 200 kDa. In certain embodiments, the number average molecular weight of the thermoresponsive polymer is greater than or equal to 1 kDa, greater than or equal to 2 kDa, greater than or equal to 5 kDa, greater than or equal to 10 kDa, greater than or equal to 25 kDa, greater than or equal to 50 kDa, greater than or equal to 75 kDa, greater than or equal to 100 kDa, greater than or equal to 125 kDa, greater than or equal to 150 kDa, or greater than or equal to 175 kDa. In certain embodiments, the number average molecular weight of the thermoresponsive polymer is less than or equal to 200 kDa, less than or equal to 175 kDa, less than or equal to 150 kDa, less than or equal to 125 kDa, less than or equal to 100 kDa, less than or equal to 75 kDa, less than or equal to 50 kDa, less than or equal to 25 kDa, less than or equal to 10 kDa, less than or equal to 5 kDa, or less than or equal to 2 kDa. Combinations of the above-referenced ranges are also possible (e.g., greater than or equal to 1 kDa and less than or equal to 200 kDa, greater than or equal to 5 kDa and less than or equal to 100 kDa). Other ranges and combinations are also possible.

Without wishing to be bound by theory, ligands having a functional group comprising sulfonic acids, sulfates, phosphonic acids, phosphates, or derivatives thereof may be particularly suitable for selectively binding to sites of inflammation at a location internal to a subject as, for example, such sites typically exhibit increased net positive charge(s) as compared to otherwise healthy tissue at the same location.

In some embodiments, the ligand may be polyfunctional. That is to say, the thermoresponsive polymer and/or one or more ligands may be reacted with a dendrimer such that the ligand is polyfunctional. For example, in some embodiments, the thermoresponsive polymer may be reacted with a dendrimer such as an acetylene-(2,2-)bismethylolpropionic acid (bis-MPA-acetylene core) comprising dendrimer.

In some embodiments, the dendrimer comprises a bis-MPA dendritic system e.g., with an acetylene core. In certain embodiments, the dendrimer has a structure as in Formula (III):

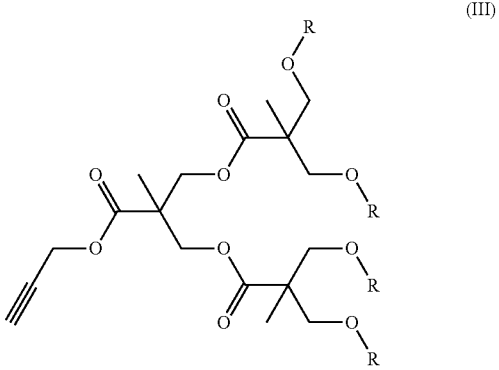

wherein each R is the same or different and is hydrogen or comprises bismethylolpropionic acid (e.g., —COC(CH$_3$)(CH$_2$OR')$_2$), 4-oxobutanoic acid (e.g., —CO(CH$_2$)$_2$COOH), or derivatives thereof. In some embodiments, each R' is the same or different and is hydrogen or comprises bismethylolpropionic acid (e.g., —COC(CH$_3$)(CH$_2$OR')$_2$), 4-oxobutanoic acid (e.g., —CO(CH$_2$)$_2$COOH), or derivatives thereof. Additional suitable dendrimers can be found, for example, in Carlmark, Anna, Eva Malmström, and Michael Malkoch, "*Dendritic architectures based on bis-MPA: functional polymeric scaffolds for application-driven research*" Chemical Society Reviews 42.13 (2013): 5858-5879, which is incorporated herein by reference in its entirety. Those of ordinary skill in the art would be capable of selecting suitable dendrimers for forming polyfunctional ligands based upon the teachings of this specification.

Figure 2B:
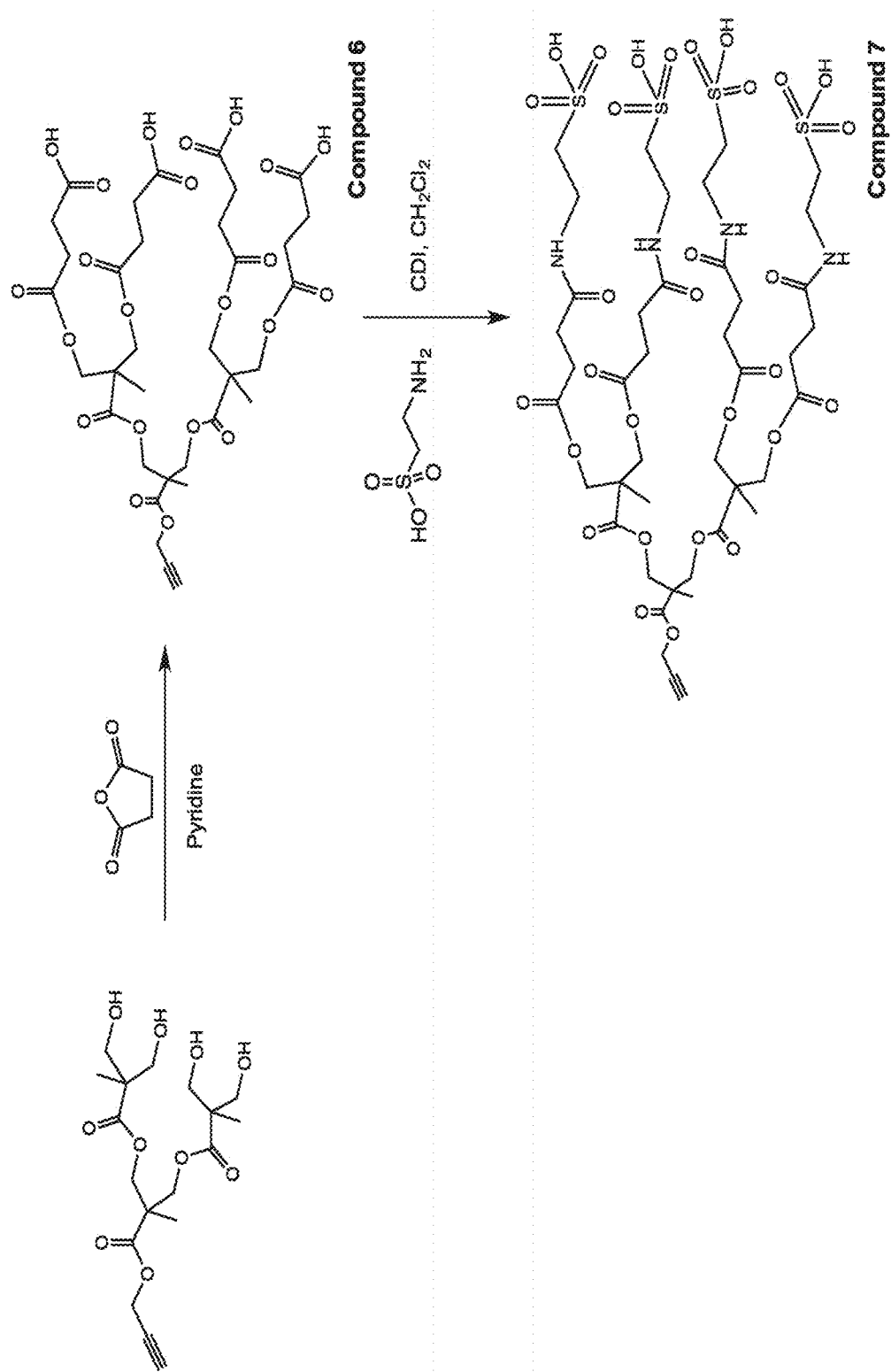
FIG. 2B is a chemical reaction scheme for forming an exemplary thermoresponsive composition, according to one set of embodiments.
Figure 2C:
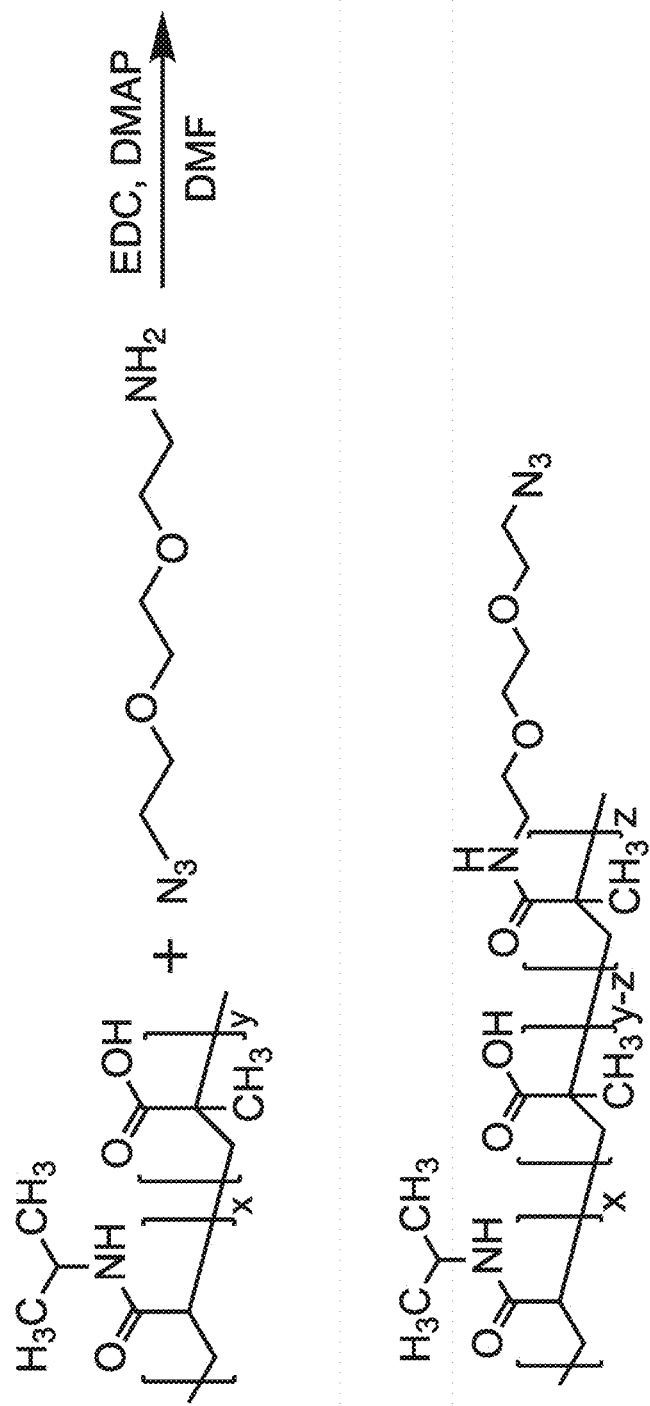
FIG. 2C is a chemical reaction scheme for forming an exemplary thermoresponsive composition, according to one set of embodiments.
Figure 2D:
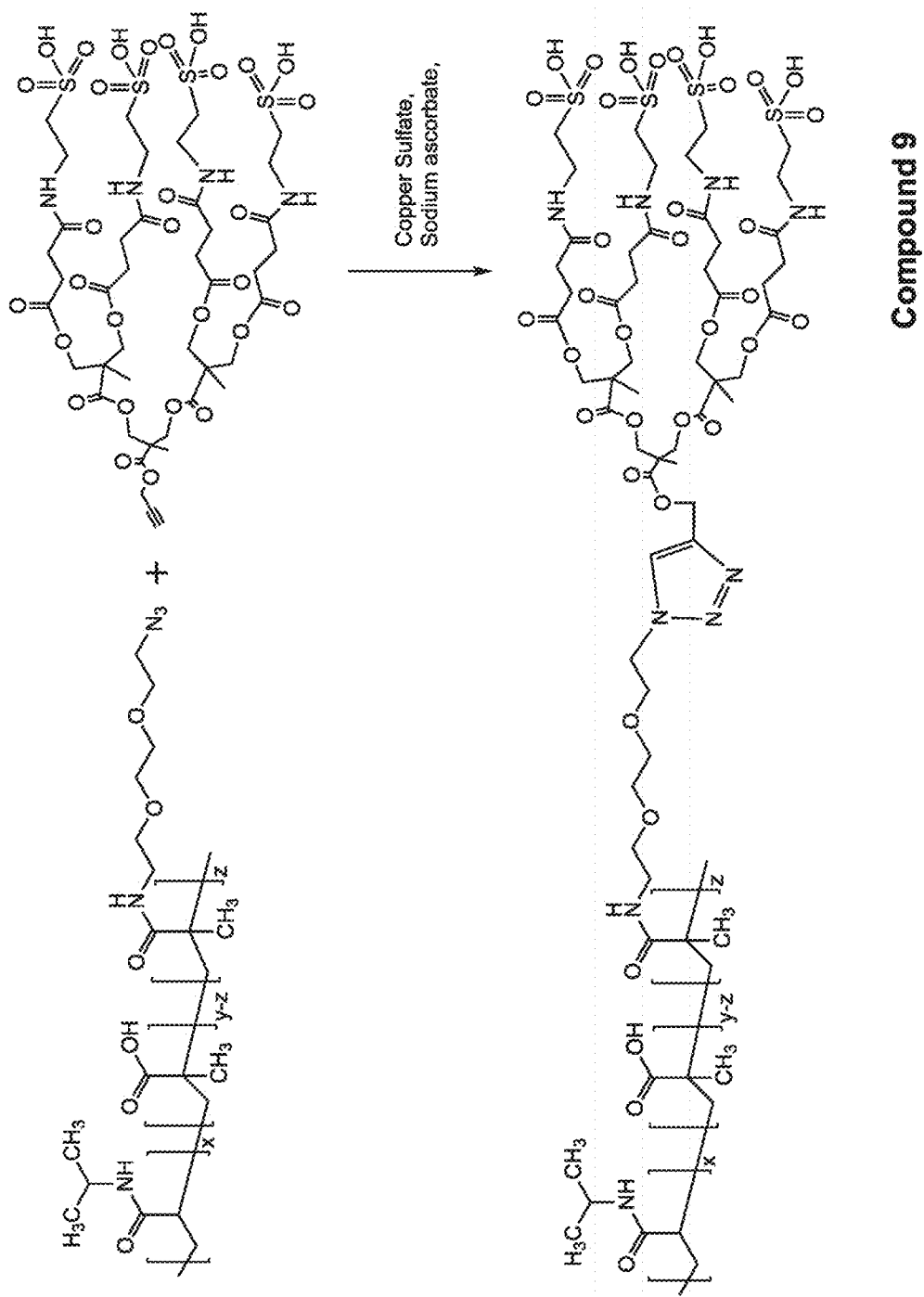
FIG. 2D is a chemical reaction scheme for forming an exemplary thermoresponsive composition, according to one set of embodiments.

For example, as illustrated in FIGS. 2B-2D, an exemplary dendrimer (e.g., Compound 6 in FIG. 2B) may be reacted with a ligand to form a polyfunctional ligand (e.g., Compound 7 in FIG. 2B). The polyfunctional ligand, in some cases, may then be reacted (e.g., via a 'click' chemistry reaction) with the thermoresponsive polymer to form a polyfunctional thermoresponsive polymer (e.g., Compound 9 in FIG. 2D). In some embodiments, at least a portion of the second monomer reacts with the polyfunctional ligand to form the polyfunctional thermoresponsive polymer. In certain embodiments, the ligand is polyfunctional and comprises two or more compounds selected from the group consisting of N,N-dimethyl-ethylenediamine, taurine, 2-aminoethyl hydrogen sulfate, O-phosphorylethanolamine, 2-aminoethyl-phosphonic acid, and derivatives thereof.

Without wishing to be bound by theory, the adhesion of the thermoresponsive polymer to the location internal to the subject may be controlled (i.e. tuned) by e.g., varying the concentration of the functional group present on the thermoresponsive polymer (e.g., by varying the concentration of ligand reacted with the thermoresponsive polymer, by varying the functionality of the dendrimer-ligand).

In some embodiments, the thermoresponsive polymer may adhere and be retained at a location internal to a subject (e.g., on inflamed tissue) for a particular length of time. In some embodiments, the thermoresponsive polymer is retained at the location internal to the subject for greater than or equal to 10 min, greater than or equal to 15 minutes, greater than or equal to 30 minutes, greater than or equal to 60 minutes, greater than or equal to 90 minutes, or greater than or equal to 120 minutes. In certain embodiments, the thermoresponsive polymer is retained at the location internal to the subject for less than or equal to 240 minutes, less than or equal to 120 minutes, less than or equal to 90 minutes, less than or equal to 60 minutes, less than or equal to 30 minutes, or less than or equal to 15 minutes. Combinations of the above-referenced ranges are possible (e.g., greater than or equal to 10 minutes and less than or equal to 240 minutes). Other ranges and combinations are also possible.

The thermoresponsive polymers described herein may have a particular lower critical solution temperature (LCST). As described above, in some embodiments, the thermoresponsive polymer may be in solution below the LCST (e.g., at ambient conditions) and, upon reaching physiological conditions (e.g., at a temperature above the LCST), undergoes a sol-to-gel transition. Advantageously, the thermoresponsive polymers described herein may be administered to a subject in solution form and, upon reaching physiological conditions, undergoes a sol-to-gel transition and adheres to a location internal to the subject in a gel state (i.e. forms a hydrogel polymer). In some embodiments, after undergoing the sol-to-gel transition, the thermoresponsive polymer may be characterized as a hydrogel polymer.

In some embodiments, the LCST of the thermoresponsive polymer is greater than or equal to 32° C., greater than or equal to 33° C., greater than or equal to 34° C., greater than or equal to 35° C., greater than or equal to 36° C., greater than or equal to 37° C., greater than or equal to 38° C., greater than or equal to 39° C., greater than or equal to 40° C., or greater than or equal to 41° C. In certain embodiments, the LCST of the thermoresponsive polymer is less than or equal to 42° C., less than or equal to 41° C., less than or equal to 40° C., less than or equal to 39° C., less than or equal to 38° C., less than or equal to 37° C., less than or equal to 36° C., less than or equal to 35° C., less than or equal to 34° C., or less than or equal to 33° C. Combinations of the above-referenced ranges are possible (e.g., greater than or equal to 32° C. and less than or equal to 42° C.). Other ranges and combinations are also possible.

That is to say, in some embodiments, the thermoresponsive polymer undergoes a sol-to-gel transition at a temperature greater than or equal to 32° C., greater than or equal to 33° C., greater than or equal to 34° C., greater than or equal to 35° C., greater than or equal to 36° C., greater than or equal to 37° C., greater than or equal to 38° C., greater than or equal to 39° C., greater than or equal to 40° C., or greater than or equal to 41° C. In certain embodiments, the thermoresponsive polymer undergoes a sol-to-gel transition at a temperature less than or equal to 42° C., less than or equal to 41° C., less than or equal to 40° C., less than or equal to 39° C., less than or equal to 38° C., less than or equal to 37° C., less than or equal to 36° C., less than or equal to 35° C., less than or equal to 34° C., or less than or equal to 33° C. Combinations of the above-referenced ranges are possible (e.g., greater than or equal to 32° C. and less than or equal to 42° C.). Other ranges and combinations are also possible.

In some embodiments, the thermoresponsive polymer may be removed from the location internal to the subject by, for example, exposing the thermoresponsive polymer to a solution (e.g., water) having a temperature less than the LCST of the thermoresponsive polymer. In certain embodiments, the thermoresponsive polymer may be chemically reacted with a solution that dissolves the hydrogel, such that the thermoresponsive polymer may be removed from the subject.

In some embodiments, the thermoresponsive polymer may be designed to have a particular viscosity. In certain embodiments, the viscosity of the thermoresponsive polymer may be controlled (i.e. tuned) by the addition of one or more excipients. In some embodiments, the excipient comprises a hydrophilic polymer. Non-limiting examples of suitable hydrophilic polymers include hydroxyl-containing polysaccharides such as dextran and hydroxyethylcellulose. Without wishing to be bound by theory, increasing the viscosity of the thermoresponsive polymer may, in some cases, increase the retention time of the thermoresponsive polymer (e.g., at the location internal to the subject) and/or reduce diffusion of undesired contaminants (e.g., pathogens, toxins) into the thermoresponsive polymer relative to a thermoresponsive polymer absent the excipient.

As described above, in some embodiments, the therapeutic agent may be associated with a nanoparticle. In certain embodiments, the therapeutic agent may be encapsulated by the nanoparticle. In some cases, the therapeutic agent may be embedded within (e.g., within a matrix of) the nanoparticle. The nanoparticle may be administered to a subject, as described herein, either directly or dispersed within the solution comprising the thermoresponsive polymer. In embodiments in which the nanoparticle is administered directly, the nanoparticle may selectively adhere to a (surface of a) location internal to a subject e.g., that is a site of inflammation. In embodiments in which the nanoparticle is administered in the solution comprising the thermoresponsive polymer, the nanoparticle may be released from the thermoresponsive polymer upon adhesion of the thermoresponsive polymer to (a surface of) the location internal to the subject. As described herein, a therapeutic agent may be released from the nanoparticle e.g., at the location internal to the subject.

The nanoparticles may comprise any suitable material (e.g., for the shell of the nanoparticle) for encapsulating and/or embedding and releasing a therapeutic agent (e.g., at a location internal to the subject). Non-limiting examples of suitable materials include poly(lactic-co-glycolic acid), poly(thioketal), poly(lactic acid), or the like.

In certain embodiments, the therapeutic agent may be dispersed in an aqueous phase (e.g., water) within the nanoparticle. In some cases, the therapeutic agent however may be dispersed in a non-aqueous phase (e.g., oil) within the nanoparticle.

In some embodiments, the nanoparticles may comprise biopolymers such as proteins (e.g., albumin such as human serum albumin, collagen, gelatin, silk, zein, beta-casein, derivatives thereof, and/or combinations thereof), protein-mimicked polypeptides, and/or polysaccharides (e.g., dextran, hydroxyethylcellulose, chitosan, alginate, pullulan, starch, derivatives thereof, and/or combinations thereof). In a particular set of embodiments, the nanoparticles comprises albumin (e.g., human serum albumin). In certain embodiments, a shell or a matrix of the nanoparticle which encapsulates and/or comprises the therapeutic agent may comprise albumin (e.g., human serum albumin). In a particular set of embodiments, the nanoparticles comprises a matrix comprising albumin and a therapeutic agent associated with the matrix.

In certain embodiments, the nanoparticles may comprise a coating (e.g., a coating on a surface of the nanoparticle). In some embodiments, the coating comprises a negatively charged biopolymer. In a particular set of embodiments, the coating comprises heparin. Without wishing to be bound by theory, heparin may increase the adhesion of the nanoparticle to a site of inflammation (e.g., such that the therapeutic agent encapsulated within the nanoparticle may be released to the site of inflammation) as compared to nanoparticles without such a coating. The inventors unexpectedly discovered that nanoparticles comprising albumin coated with heparin may be suitable (e.g., is stable for encapsulating therapeutic agents) for delivery to locations internal to a subject including, for example, the gastrointestinal tract. By contrast, and without wishing to be bound by theory, it would have otherwise been previously expected that given the rich protease environment of the GI tract, nanoparticles formulated from albumin may have been degraded too quickly to serve as an effective therapeutic agent delivery vehicle.

In some cases, an antibody and/or aptamer may be functionalized on the surface of a nanoparticle (e.g., bound to the coating, bound to the matrix). Those of ordinary skill in the art would understand how to bind an antibody and/or aptamer to the surface of a nanoparticle, based upon the teachings of this specification.

In some embodiments, the nanoparticles may have an maximum cross-sectional dimension (e.g., diameter) of greater than or equal to 100 nm and less than or equal to 1000 nm. In certain embodiments, the maximum cross-sectional dimension of the nanoparticle is greater than or equal to 100 nm, greater than or equal to 150 nm, greater than or equal to 200 nm, greater than or equal to 300 nm, greater than or equal to 400 nm, greater than or equal to 500 nm, greater than or equal to 600 nm, greater than or equal to 700 nm, greater than or equal to 800 nm, or greater than or equal to 900 nm. In certain embodiments, the maximum cross-sectional dimension of the nanoparticle is less than or equal to 1000 nm, less than or equal to 900 nm, less than or equal to 800 nm, less than or equal to 700 nm, less than or equal to 600 nm, less than or equal to 500 nm, less than or equal to 400 nm, less than or equal to 300 nm, less than or equal to 200 nm, or less than or equal to 150 nm. Combinations of the above-referenced ranges are also possible (e.g., greater than or equal to 100 nm and less than or equal to 1000 nm, greater than or equal to 200 nm and less than or equal to 1000 nm). Other ranges and combinations are also possible. The maximum cross-sectional dimension of a nanoparticle may be determined using scanning electron microscopy (SEM).

In certain embodiments, the nanoparticles may have a polydispersity index (PDI) of less than or equal to 0.2, less than or equal to 0.15, less than or equal to 0.1, less than or equal to 0.05, less than or equal to 0.02, or less than or equal to 0.01. In some embodiments, the nanoparticles may have a polydispersity index of greater than or equal to 0, greater than or equal to 0.01, greater than or equal to 0.02, greater than or equal to 0.05, greater than or equal to 0.1, or greater than or equal to 0.15. Combinations of the above-referenced ranges are also possible (e.g., less than or equal to 0.2 and greater than or equal to 0).

Nanoparticles described herein may have a particular shape as defined by a cross-sectional area of the nanoparticle. Non-limiting examples of suitable cross-sectional shapes include square, circles, ovals, polygons (e.g., pentagons, hexagons, heptagons, octagons, nonagons, dodecagons, or the like), tubes, rings, star or star-like/stellate, or the like. Those skilled in the art would be capable of selecting suitable shapes depending on the application and based upon the teachings of this specification.

In some embodiments, one or more therapeutic agents may be associated with the thermoresponsive polymer (hydrogel) and/or nanoparticles. In some embodiments, the therapeutic agent(s) may be embedded within (e.g., dispersed within) the thermoresponsive polymer. In certain embodiments, the therapeutic agent(s) may be embedded within and/or encapsulated within a nanoparticle. In some cases, the nanoparticle may be associated with the thermoresponsive polymer material. In some cases, the therapeutic agent may be associated with the thermoresponsive polymer through a chemical bond. Representative bond types include covalent and ionic. In certain embodiments, the therapeutic agent is covalently bonded to the thermoresponsive polymer. In some embodiments, the therapeutic agent is bonded to the polymeric material through a carboxylic acid derivative. In some cases, the carboxylic acid derivative may be an ester bond. For example, therapeutic agents that contain a carboxylic acid group may be directly incorporated into thermoresponsive polymer materials that contain ester and hydroxyl groups without further modification. Therapeutic agents containing an alcohol may first be derivatized as a succinic or fumaric acid monoester and then incorporated into the thermoresponsive polymer material. Therapeutic agents that contain a thiol may be incorporated into olefin or acetylene-containing thermoresponsive polymers through a sulfur-ene reaction. In some cases, the therapeutic agent comprises an amine functional group capable of reacting with an epoxide functional group (e.g., on a polyfunctional monomer) to form an amide or ester bond. In other embodiments, the one or more therapeutic agents are non-covalently associated with the thermoresponsive polymer (e.g., dispersed or encapsulated within). In some such embodiments, the therapeutic agent may be dispersed or encapsulated within the thermoresponsive polymer or nanoparticles by hydrophilic and/or hydrophobic forces.

In certain embodiments, the composition is constructed and arranged to release the therapeutic agent from the thermoresponsive polymer (hydrogel) and/or nanoparticles (e.g., the therapeutic agent is released from the hydrogel and/or nanoparticles upon reaching a desired location internal to the subject such as a site of inflammation). Such embodiments may be useful in the context of drug delivery.

As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Therapeutic agents include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. In some embodiments, the therapeutic agent may be selected from "Approved Drug Products with Therapeutic Equivalence and Evaluations," published by the United States Food and Drug Administration (F.D.A.) (the "Orange Book"). In some cases, the therapeutic agent is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In certain embodiments, the therapeutic agent is a small molecule. Exemplary classes of agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents (e.g., taxanes, such as paclitaxel and docetaxel; cisplatin, doxorubicin, methotrexate, etc.), antihistamines, antimigraine drugs, hormones, prostaglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, antiasthma drugs, cardiovascular drugs, anesthetics, anticoagulants, inhibitors of an enzyme, steroidal agents, steroidal or non-steroidal anti-inflammatory agents, corticosteroids (e.g., budesonide, prednisone, hydrocortisone, triamcinolone, dexamethasone), immunomodulatory drugs (e.g., anti-TNFs, integrin inhibitors, IL-23 inhibitors, GMCSF, IL10), dopaminergics, electrolytes, gastro-intestinal drugs, muscle relaxants, nutritional agents, vitamins, parasympathomimetics, stimulants, anorectics and anti-narcoleptics. Nutraceuticals can also be incorporated. These may be vitamins, supplements such as calcium or biotin, or natural ingredients such as plant extracts or phytohormones.

In some embodiments, the therapeutic agent is a radiopaque material such as tungsten carbide or barium sulfate. In certain embodiments, the therapeutic agent is a radio-pharmaceutical (e.g., comprising carbon-11, carbon-14, fluorine-18, gallium-67, indium-111, iodine-123, iodine-125, iodine-131, molybdenum-99, radium-223, technetium-99, thallium-201, yttrium-90).

In another embodiment, the therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell recepotors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In an exemplary embodiment, the therapeutic agent is granulocyte macrophage colony-stimulating factor (GM-CSF).

In a further embodiment, the therapeutic agent is an antimicrobial agent. Exemplary antimicrobials include antibiotics such as aminoglycosides, cephalosporins, chloramphenicol, clindamycin, erythromycins, fluoroquinolones, macrolides including fidaxomicin and rifamycins such as rifaximin, azolides, metronidazole, penicillins, tetracyclines, trimethoprim-sulfamethoxazole, oxazolidinone such as linezolid, and glycopeptides such as vancomycin. Other antimicrobial agents include antifungals such as antifungal polyenes such as nystatin, amphotericin, candicidin and natamycin, antifungal azoles, allylamine antifungals and echinocandins such as micafungin, caspofungin and anidulafungin.

In some embodiments, the therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In other embodiments, the therapeutic agent is a protein or other biological macromolecule.

In some embodiments, as described herein, the therapeutic agent may be loaded into a nanoparticle prior to formation of the hydrogel. Such loading permits encapsulation of therapeutic agents (e.g., relatively large macromolecule therapeutic agents) that couldn't otherwise be easily loaded into a drug delivery material (e.g., in traditional thermosets and/or crosslinked polymeric materials). In certain embodiments, the therapeutic agent and/or nanoparicle is added to a solution comprising the thermoresponsive polymer prior to formation of the hydrogel. Such loading permits the administration of a solution comprising the thermoresponsive polymer, therapeutic agent, and/or nanoparticle to a subject and, upon reaching a temperature above the LCST of the thermoresponsive polymer, the therapauetic agent and/or nanoparticle are embedded within the hydrogel. In some embodiments, the therapeuetic agent and/or nanoparticles are releasable from the hydrogel. That is to say, in certain embodiments, upon reaching a location internal to the subject (e.g., such as a site of inflammation), the hydrogel may form and selectively adhere to the location, and the therapeutic agent (or nanoparticle comprising the therapeutic agent) is released from the hydrogel at the location. Advantageously, such articles and compositions may provide the targeted release of a therapeutic agent at a site of inflammation without, for example, the therapeutic agent substantially interacting with otherwise healthy tissue of the subject.

The therapeutic agent may be associated with the hydrogel and present in the composition (or article), in any suitable amount. In some embodiments, the therapeutic agent is present in the composition an amount ranging between about 0.01 wt % and about 50 wt % versus the total composition weight. In some embodiments, the therapeutic agent is present in the composition in an amount of at least about 0.01 wt %, at least about 0.05 wt %, at least about 0.1 wt %, at least about 0.5 wt %, at least about 1 wt %, at least about 2 wt %, at least about 3 wt %, at least about 5 wt %, at least about 10 wt %, at least about 20 wt %, at least about 30 wt %, at least about 40 wt % versus the total composition weight. In certain embodiments, the therapeutic agent is present in the composition in an amount of less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 3 wt %, less than or equal to about 2 wt %, less than or equal to about 1 wt %, less than or equal to about 0.5 wt %, less than or equal to about 0.1 wt %, or less than or equal to about 0.05 wt %. Combinations of the above-referenced ranges are also possible (e.g., between about 0.01 wt % and about 50 wt %). Other ranges are also possible.

The therapeutic agent may be encapsulated within a nanoparticle and present in the article, in any suitable amount. In some embodiments, the therapeutic agent is encapsulated within a nanoparticle in an amount ranging between about 0.01 wt % and about 50 wt % versus the total nanoparticle weight. In some embodiments, the therapeutic agent is encapsulated within a nanoparticle and is present in an amount of at least about 0.01 wt %, at least about 0.05 wt %, at least about 0.1 wt %, at least about 0.5 wt %, at least about 1 wt %, at least about 2 wt %, at least about 3 wt %, at least about 5 wt %, at least about 10 wt %, at least about 20 wt %, at least about 30 wt %, at least about 40 wt % versus the total nanoparticle weight. In certain embodiments, the therapeutic agent is present in the nanoparticle in an amount of less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 3 wt %, less than or equal to about 2 wt %, less than or equal to about 1 wt %, less than or equal to about 0.5 wt %, less than or equal to about 0.1 wt %, or less than or equal to about 0.05 wt % versus the total nanoparticle weight. Combinations of the above-referenced ranges are also possible (e.g., between about 0.01 wt % and about 50 wt %). Other ranges are also possible.

In certain embodiments, the therapeutic agent is released by diffusion out of the hydrogel and/or nanoparticle. In some embodiments, the therapeutic agent is released by degradation of the nanoparticle (e.g., biodegradation, enzymatic degradation, hydrolysis). In some cases, the therapeutic agent may be released be exposure of the thermoresponsive polymer (hydrogel) and/or nanoparticle associated with the therapeutic agent to a stimulis such as ultrasound and/or radiowave.

In some embodiments, the therapeutic agent is released from the hydrogel and/or nanoparticle at a particular rate. In some embodiments, between 0.05 wt % to 99 wt % of the therapeutic agent initially contained in a composition (or article) is released (e.g., in vivo) between 24 hours and 1 year. In some embodiments, between about 0.05 wt % and about 99.0 wt % of the therapeutic agent is released (e.g., in vivo) from the composition after a certain amount of time. In some embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the therapeutic agent associated with the composition is released from the composition (e.g., in vivo) within about 24 hours, within 36 hours, within 72 hours, within 96 hours, or within 192 hours. In certain embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the therapeutic agent associated with the composition is released from the composition (e.g., in vivo) within 1 day, within 5 days, within 30 days, within 60 days, within 120 days, or within 365 days. For example, in some cases, at least about 90 wt % of the therapeutic agent associated with the composition is released from the composition (e.g., in vivo) within 120 days.

In some embodiments, the therapeutic agent is released from the composition at a particular initial average rate as determined over the first 24 hours of release (the "initial rate") (e.g., release of the therapeutic agent at the desired location internally of the subject, such as an internal cavity). In certain embodiments, the therapeutic agent is released at an average rate of at least about 1%, at least about 2%, at least about 5%, least about 10%, at least about 20%, at least about 30%, least about 50%, at least about 75%, at least about 80%, at least about 90%, at least about 95%, or at least about 98% of the initial average rate over a 24 hour period after the first 24 hours of release. In some embodiments, the therapeutic agent is released at an average rate of less than or equal to about 99%, less than or equal to about 98%, less than or equal to about 95%, less than or equal to about 90%, less than or equal to about 80%, less than or equal to about 75%, less than or equal to about 50%, less than or equal to about %, less than or equal to about 30%, less than or equal to about 20%, less than or equal to about 10%, less than or equal to about 5%, or less than or equal to about 2% of the initial average rate over a 24 hour period after the first 24 hours of release. Any and all closed ranges that have endpoints within any of the above referenced ranges are also possible (e.g., between about 1% and about 99%, between about 1% and about 98%, between about 2% and about 95%, between about 10% and about 30%, between about 20% and about 50%, between about 30% and about 80%, between about 50% and about 99%). Other ranges are also possible.

The therapeutic agent may be released at an average rate over at least one selected continuous 24 hour period at a rate of between about 1% and about 99% of the initial rate between 48 hours and about 1 year (e.g., between 48 hours and 1 week, between 3 days and 1 month, between 1 week and 1 month, between 1 month and 6 months, between 3 months and 1 year, between 6 months and 2 years) after the initial release.

For example, in some cases, the therapeutic agent may be released at a rate of between about 1% and about 99% of the initial rate on the second day of release, the third day of release, the fourth day of release, the fifth day of release, the sixth day of release, and/or the seventh day of release.

In certain embodiments, burst release of an therapeutic agent from the composition is generally avoided. In an illustrative embodiment, in which at least about 0.05 wt % of the therapeutic agent is released from the composition within 24 hours, between about 0.05 wt % and about 99 wt % is released during the first day of release (e.g., at the location internally of the subject), and between about 0.05 wt % and about 99 wt % is released during the second day of release. Those skilled in the art would understand that the therapeutic agent may be further released in similar amounts during a third day, a fourth day, a fifth day, etc. depending on the properties of the composition and/or the therapeutic agent.

In certain embodiments, the therapeutic agent may be released with a pulse release profile. For example, in some embodiments, the therapeutic agent may be released on the first day after administration and during another 24 hour period such as starting during the third day, the fourth day, or the fifth day, but is not substantially released on other days. Those skilled in the art would understand that other days and/or combinations of pulsing and continuous release are also possible.

The therapeutic agent may be released at a relatively constant average rate (e.g., a substantially zero-order average release rate) over a time period of at least about 24 hours. In certain embodiments, the therapeutic agent is released at a first-order release rate (e.g., the rate of release of the therapeutic agent is generally proportional to the concentration of the therapeutic agent) of a time period of at least about 24 hours.

In some embodiments, at least a portion of the therapeutic agent loaded into the composition is released continuously (e.g., at varying rates) over the residence time period of the composition. Residence time periods are described in more detail herein.

A "subject" as used herein refers to any animal such as a mammal (e.g., a human). In some embodiments, the subject is a mammal (e.g. , a human, a non-human primate, or a non-human mammal), a vertebrate, a laboratory animal, a domesticated animal, an agricultural animal, or a companion animal. Non-limiting examples of subjects include a human, a non-human primate, a cow, a horse, a pig, a sheep, a goat, a rabbit, a goat, a dog, a cat, a rodent such as a mouse, a rat, a hamster, a bird, a fish, or a guinea pig. Generally, the invention is directed toward use with humans. In some embodiments, a subject may demonstrate health benefits, e.g., upon administration of the composition and/or article.

As used herein, the term "liquid" is given its ordinary meaning in the art. A liquid cannot maintain a defined shape and will flow during an observable time frame to fill the container in which it is put. Thus, the liquid may have any suitable viscosity that permits flow.

The phrase "associated with" as used herein means generally held in close proximity or contained within. For example, a therapeutic agent associated with a thermoresponsive polymer (hydrogel) or nanoparticle may be at least partially encapsulated (e.g., completely encapsulated) within the hydrogel or nanoparticle, may be at least partially embedded (e.g., completely embedded) within the hydrogel or nanoparticle, and/or adjacent (e.g., directly adjacent, coated onto, embedded within) a surface of the hydrogel or nanoparticle. For example, a portion of the therapeutic agent may be at least partially embedded within the hydrogel or nanoparticle material and another portion may protrude from a surface of the hydrogel or nanoparticle, in some embodiments. In a particular set of embodiments, the therapeutic agent(s) associated with the hydrogel is encapsulated within a nanoparticle(s) embedded within the hydrogel. In some cases, the therapeutic agent (or nanoparticle comprising the therapeutic agent) may be associated with a solution comprising a polymer and, upon the solution undergoing sol-to-gel transition, the therapeutic agent (or nanoparticle comprising the therapeutic agent) is associated with the resulting hydrogel.

The phrase "thermoresponsive polymer" or "thermoresponsive hydrogel" as used herein generally refers to a polymer or hydrogel which undergoes a phase transition (e.g., liquid to solid or semi-solid such as a sol-to-gel transition) at a particular temperature or range of temperatures. In some embodiments, the thermoresponsive hydrogel has a lower critical solution temperature (LCST) where, at a temperature below the LCST, the hydrogel is in liquid phase (e.g., a solution) and, at a temperature above the LCST, the hydrogel is in solid or semi-solid phase (e.g., a gel).

As used herein, the term "hydrogel" or "hydrogel polymer" is given its ordinary meaning in the art and generally refers to a network of polymer chains that are at least partially water-insoluble and are dispersed in an aqueous medium. In some cases, the hydrogel may comprise greater than or equal to 90 vol %, greater than or equal to 95 vol %, greater than or equal to 98 vol %, greater than or equal to 99 vol %, greater than or equal to 99.5 vol %, greater than or equal to 99.8 vol %, or greater than or equal to 99.9 vol % water versus the total hydrogel polymer composition.

The phrase "inflamed tissue" or "site of inflammation" are given their ordinary meaning in the art and one of ordinary skill in the art would be capable of determining whether tissue of a subject is inflamed (i.e. is a site of inflammation) based upon the teachings of this specification. For example, in colonic mucosa, inflammation may be characterized by 1) a depletion of the mucus layer and in situ accumulation of positively charged proteins including transferrin, bactericidal/permeability-increasing protein, and antimicrobial peptides; 2) up-regulation and release of degradative enzymes including, for example, esterases and/or matrix metalloproteinases (MMPs); and/or 3) increased tissue permeability as compared to otherwise healthy colonic mucosa. One of ordinary skill in the art would also be capable of selecting suitable methods for quantifying mucus depletion, up-regulation and/or release of enzymes, and tissue permeability, particularly in view of the teachings of this specification.

As used herein, the term "react" or "reacting" refers to the formation of a bond between two or more compounds to produce a stable, isolable compound. For example, a first compounds (e.g., monomer, ligand) and a second compound (e.g., monomer, ligand) may react to form one reaction product comprising the first compound and the second compound joined by e.g., a covalent bond. The term "reacting" may also include the use of solvents, catalysts, bases, ligands, or other materials which may serve to promote the occurrence of the reaction between compound(s). A "stable, isolable compound" refers to isolated reaction products and does not refer to unstable intermediates or transition states.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R'") wherein R', R", and R'" each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heterocycle" or "heterocyclyl" refers to a monocyclic or polycyclic heterocyclic ring that is either a saturated ring or an unsaturated non-aromatic ring. Typically, the heterocycle may include 3-membered to 14-membered rings. In some cases, 3-membered heterocycle can contain up to 3 heteroatoms, and a 4- to 14-membered heterocycle can contain from 1 to about 8 heteroatoms. Each heteroatom can be independently selected from nitrogen, which can be quaternized; oxygen; and sulfur, including sulfoxide and sulfone. The terms "heterocycle" or "heterocyclyl" may include heteroaromatic or heteroaryl groups, as described more fully below. The heterocycle may be attached via any heteroatom ring atom or carbon ring atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halogen atom, an alkyl radical, or aryl radical).

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

As used herein, the term "backbone" refers to the atoms and bonds through which the monomer units of a polymer are bound together. As used herein, the term "pendent group," when used in the context of a polymer strand, refers to functional groups which are attached to the strand but do not participate in the bonds through which the monomer units are joined. As used herein, the term "strand" refers to an oligomeric or polymeric chain of one monomer unit, or an oligomeric or polymeric chain of two or more different monomer units.

As used herein, the term "crosslink" refers to a connection between two strands. The crosslink may either be a chemical bond, a single atom, or multiple atoms. The crosslink may be formed by reaction of a pendant group in one strand with the backbone of a different strand, or by reaction of one pendant group with another pendant group. Crosslinks may exist between separate strand molecules, and may also exist between different points of the same strand.

As used herein, the terms "oligomer" and "polymers" each refer to a compound of a repeating monomeric subunit. Generally speaking, an "oligomer" contains fewer monomeric units than a "polymer." Those of skill in the art will appreciate that whether a particular compound is designated an oligomer or polymer is dependent on both the identity of the compound and the context in which it is used.

One of ordinary skill will appreciate that many oligomeric and polymeric compounds are composed of a plurality of compounds having differing numbers of monomers. Such mixtures are often designated by the average molecular weight of the oligomeric or polymeric compounds in the mixture. As used herein, the use of the singular "compound" in reference to an oligomeric or polymeric compound includes such mixtures.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkoxy" refers to an alkyl group, as defined above, having an oxygen atom attached thereto. Representative alkoxy groups include methoxy, ethoxy, propyloxy, and tert-butoxy. An "ether" is two hydrocarbons covalently linked by an oxygen.

The term "alkylthio" refers to an alkyl group, as defined above, having a sulfur atom attached thereto. In some embodiments, the "alkylthio" moiety is represented by one of —S-alkyl, —S-alkenyl, and —S-alkynyl. Representative alkylthio groups include methylthio and ethylthio.

The term "amido" is art-recognized as an amino substituted by a carbonyl group.

The term "aralkyl", as used herein, refers to an alkyl group substituted with an aryl group. The term "heteroaralkyl", as used herein, refers to an alkyl group substituted with a heteroaryl group.

The term "heteroatom" as used herein means an atom of any element other than carbon or hydrogen. Examplary heteroatoms are nitrogen, oxygen, and sulfur.

As used herein, the term "thiol" means —SH and the term "hydroxyl" means —OH.

As used herein the term "oxo" refers to a carbonyl oxygen atom.

As used herein, the term "alkaloid" refers to a naturally occurring organic compound containing at least one non-peptidic nitrogen atom.

"Nanoparticle," as used herein, generally refers to a particle of any shape having an average diameter from about 1 nm up to, but not including, about 1 micron, about 5 nm to about 500 nm, or about 5 nm to about 300 nm. In some embodiments, the particles have an average diameter from about 100 nm to about 300 nm, about 100 nm to about 250 nm, or about 100 nm to about 200 nm. Nanoparticles having a spherical shape are generally referred to as "nanospheres", although other shapes are possible.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

EXAMPLES

The following examples are intended to illustrate certain embodiments of the present invention, but do not exemplify the full scope of the invention.

In particular, the following example demonstrates a thermo-responsive, inflammation-targeting (TRIT) drug delivery system e.g., for improved enema therapies. The general concept is to administer a drug of choice embedded in a "smart" polymer that is liquid at room temperature, but undergoes gelation at body temperature to form "drug depots" at the inflamed mucosal surface for sustained drug release. In one example, a thermoresponsive polymer based on poly(N-isopropylacrylamide) (PNIPAM), which is biocompatible, is used and can be designed to gel in situ at 37° C. To achieve targeted delivery, the PNIPAM was modified with ligands so that it selectively adheres to inflamed regions of the colonic mucosa. Using unique one-on-one (e.g., monofunctional) and multiple-on-one approaches (e.g., polyfunctional), the thermo-responsive polymers were functionalized with different entities for tunable charge densities, and constructed a library of the synthesized polymers for in vivo evaluation of the selective adhesion and in situ gelation at ulcers in animal models.

To further control drug release, therapeutic agents were loaded first into nanoparticles, which were then embedded in the thermoresponsive polymer (hydrogel). The nanoparticles were formulated in such a way that small-molecule drugs (steroid, e.g., budesonide) and biological drugs (e.g., granulocyte macrophage colony-stimulating factor) can be loaded in combination, which provides a general platform for drug combination. The nanoparticles were also designed to selectively adhere to the inflamed tissue such as the colonic mucosa for local drug release at ulcers. The size of the nanoparticles were selected to provide high drug loading while maintaining selective adhesion to colonic ulcers. The PNIPAM-based polymers possess the properties of thermo-responsiveness and undergo sol-gel translation, tunable charge densities, nanoparticle-in-hydrogel for drug loading combination.

Figure 2E:
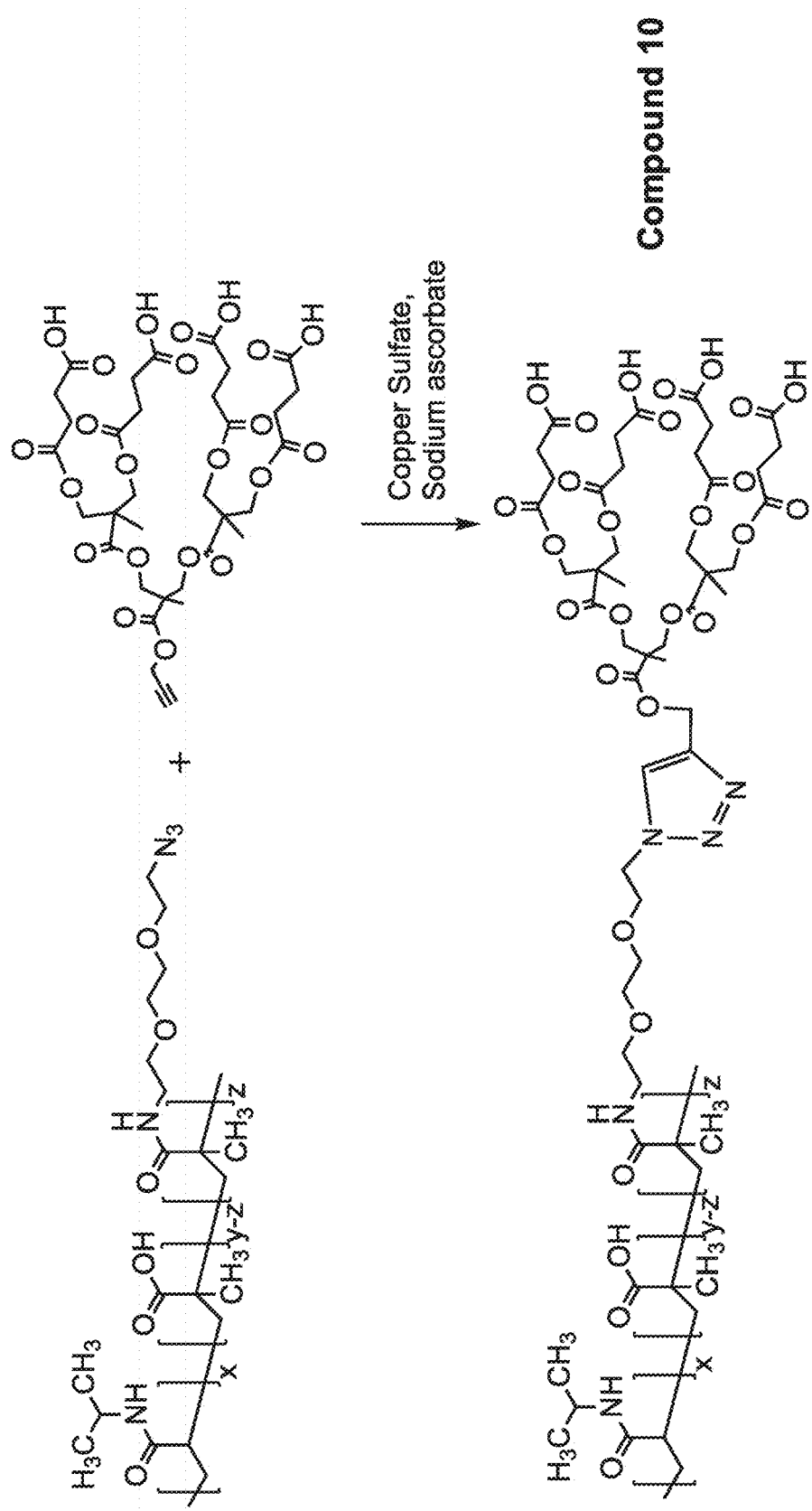
FIG. 2E is a chemical reaction scheme for forming a comparative thermoresponsive composition, according to one set of embodiments.

FIG. 1 shows an exemplary scheme starting with a thermo-responsive polymer PNIPAM-MAA, functionalizing the polymer by reacting the carboxylic acid groups with taurine for a one-on-one approach, or a Dendron-taurine for a multiple-on-one approach. FIG. 2A-2D shows exemplary EDC/NHS chemistry used to conjugate taurine to PNIPAM-MAA. A small library of 5 different ligands was conjugated to PNIPAM-MAA to compare the charge effect on polymer hydrogel adhesion to the inflamed intestine. FIG. 2B-2D shows exemplary schemes of synthesis of PNIPAM-Dendron-Taurine. FIG. 2B shows the synthesis of Dendron-Taurine (Compound 6) from commercially available Dendron. FIG. 2C shows PNIPAM-MAA was coupled to Azido-amine (Compound 8). FIG. 2D shows PNIPAM-azide was reacted with Dendron-Taurine through click chemistry. PNIPAM-azide was reacted with Dendron-acid to form PNIPAM-Dendron acid as a control compound (FIG. 2E).

Figures 3G, 3H, 3I:
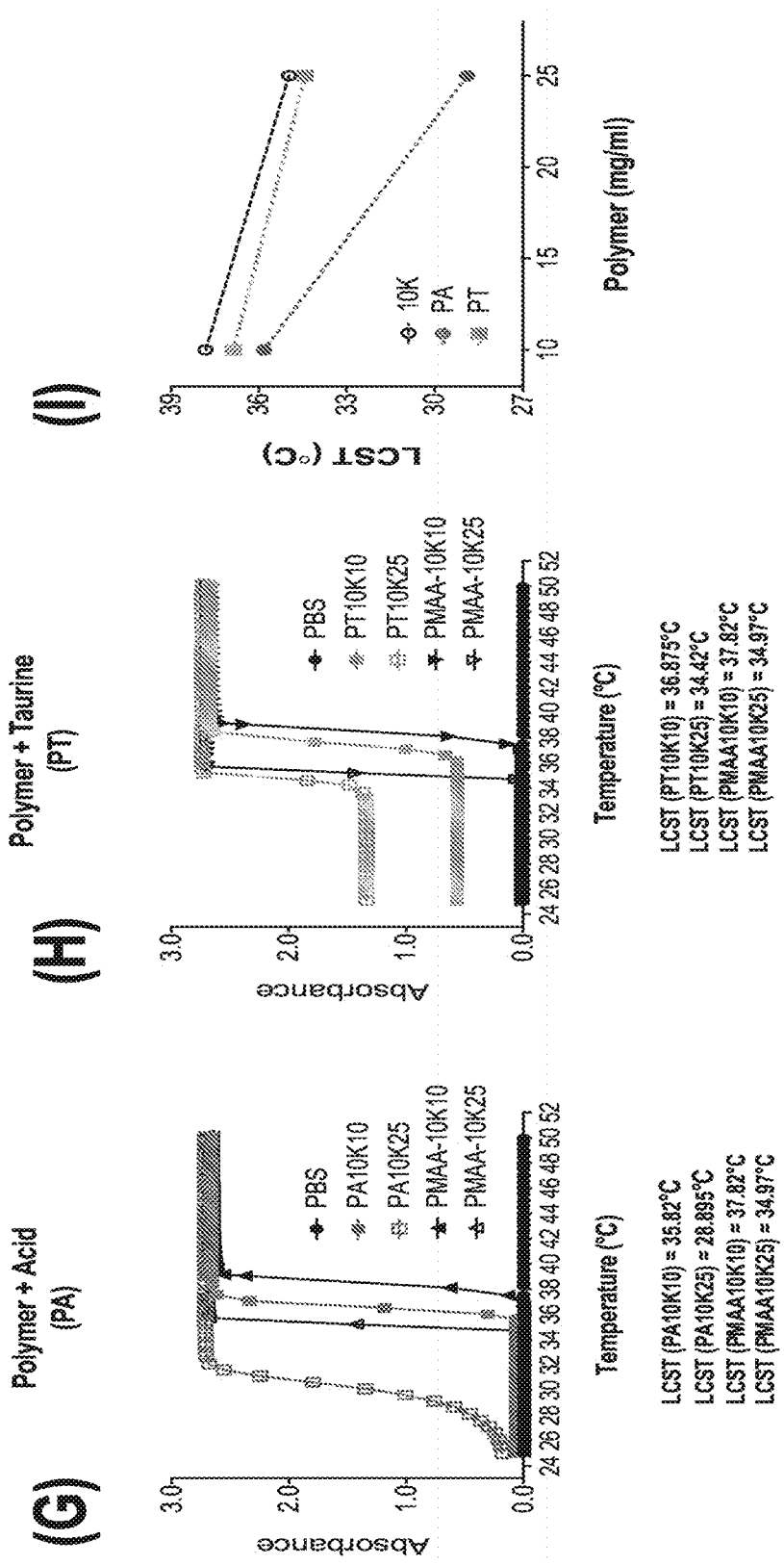
FIG. 3G is a plot of absorbance versus temperature for control hydrogel PNIPAM-Dendron acid (PA) and exemplary PNIPAM-MAA (PMAA), according to one set of embodiments.
FIG. 3H is a plot of absorbance versus temperature for PNIPAM-Dendon acid-Taurine (PT) and PNIPAM-MAA (PMAA), according to one set of embodiments.
FIG. 3I is a plot of LCST for PA, PT, and PMAA (10K), according to one set of embodiments.
Figure 4A:
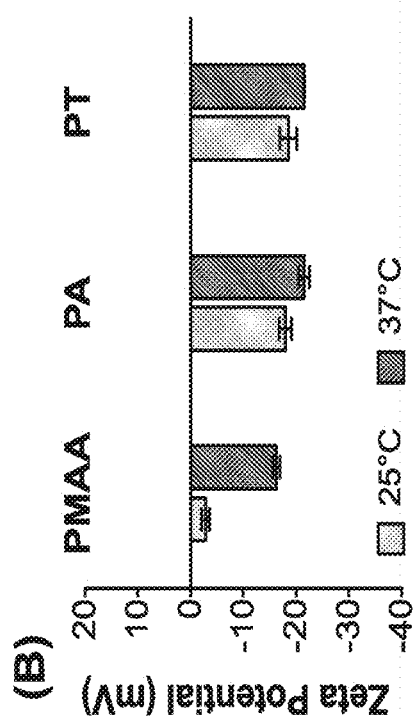
FIG. 4A is a plot of average zeta (nm) at pH=5.6 for PMAA, PA, and PT at 25° C. and 37° C., according to one set of embodiments.
Figure 4B:
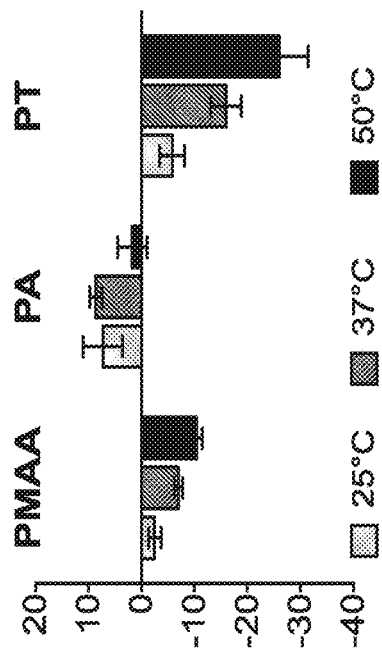
FIG. 4B is a plot of zeta potential (mV) at pH=5.6 for PMAA, PA, and PT at 25° C. and 37° C., according to one set of embodiments.
Figure 4C:
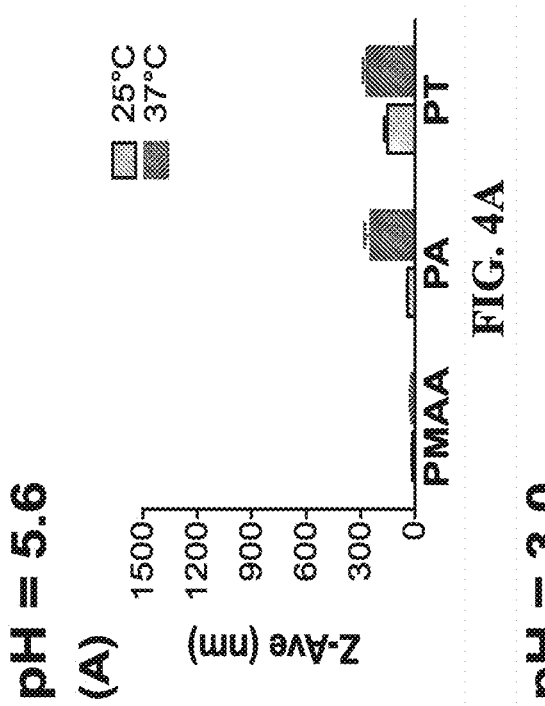
FIG. 4C is a plot of average zeta (nm) at pH=3.0 for PMAA, PA, and PT at 25° C., 37° C., and 50° C. according to one set of embodiments.
Figure 4D:
FIG. 4D is a plot of zeta potential (mV) at pH=3.0 for PMAA, PA, and PT at 25° C., 7° C., and 50° C., according to one set of embodiments.

FIG. 3 shows the transmittance % was measured as a function of temperature for different polymers. (FIG. 3A) 60 k PNIPAM-MAA in PBS at a concentration of 10, 25, 50 and 100 mg/ml was used for the measurement. PBS was measured alone as control. (FIG. 3B) 10 k PNIPAM-MAA in PBS at a concentration of 10, 25, 50 and 100 mg/ml was used for the measurement. PBS was measured alone as control. (FIG. 3C) Comparison of the lower critical solution temperature (LCST) for 60 k and 10 k PNIPAM-MAA. The LCST of each polymer solution was calculated by taking the first derivative of the transmittance curve and the peak value was used as LCST for the polymer. (FIG. 3D) The effect of 10 k dextran addition on the LCST of 60 k PNIPAM-MAA. (FIG. 3E) The effect of 70 k dextran addition on the LCST of 60 k PNIPAM-MAA. (FIG. 3F) Comparison of LCST for the addition of 10 k and 70 k dextran to 60 k PNIPAM-MAA polymer solution. (Note to samples: 60 k10+PBS: 60 k PNIPAM-MAA at 10 mg/ml in PBS; 60 k10+10kdxtl: 60 k PNIPAM-MAA at 10 mg/ml with 10 k dextran at 1 mg/ml in PBS). (FIG. 3G) The absorbance measurement of PNIPAM-Dendron acid (PA). PA solution in PBS at a concentration of 10 and 25 mg/ml was used for the measurement in comparison with PNIPAM-MAA at the same concentration. (FIG. 3H) The absorbance measurement of PNIPAM-Dendron-Taurine (PT). PT solution in PBS at a concentration of 10 and 25 mg/ml was used for the measurement in comparison with PNIPAM-MAA at the same concentration. (FIG. 3I) LCST comparison of PA, PT and the unmodified PNIPAM-MAA. (Note: PMAA indicated PNIPAM-MAA in the figure labeling).

FIGS. 4A-4D show size and zeta measurement of different hydrogel formulations. The size and zeta potential measurement of different polymers under pH=5.6 and 3.0. (FIG. 4A) All polymers, PA, PT and PNIPAM-MAA were dissolved at 0.05% in 1 mM of NaCl for the size measurement at 25° C. and 37° C. (FIG. 4B) The same polymer solutions in (FIG. 4A) were then measured for the zeta potential at 25° C. and 37° C. To simulate the inflamed acidic environment, the size (FIG. 4C) and zeta potential (FIG. 4D) of the above prepared polymer solutions were also measured under pH=3.0 at 25° C., 37° C., and 50° C.

Figure 5A:
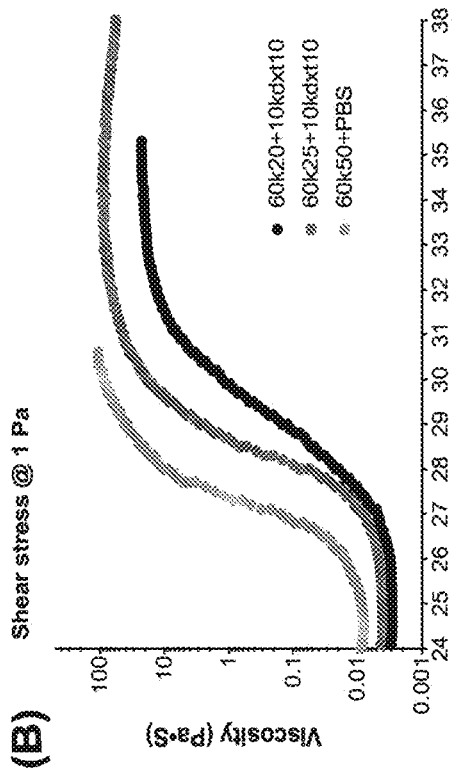
FIG. 5A is a plot of viscosity (Pa·s) versus shear rate for exemplary PNIPAM-MAA hydrogels at 37° C., according to one set of embodiments.
Figure 5B:
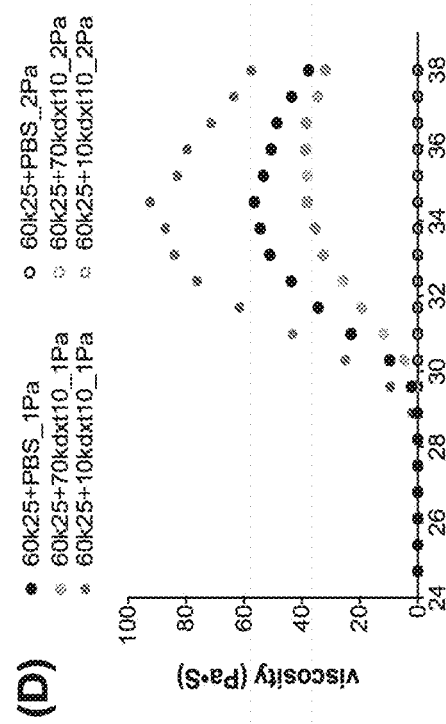
FIG. 5B is a plot of viscosity (Pa·s) versus temperature for exemplary PNIPAM-MAA hydrogels at a constant shear stress of 2 Pa, according to one set of embodiments.
Figure 5C:
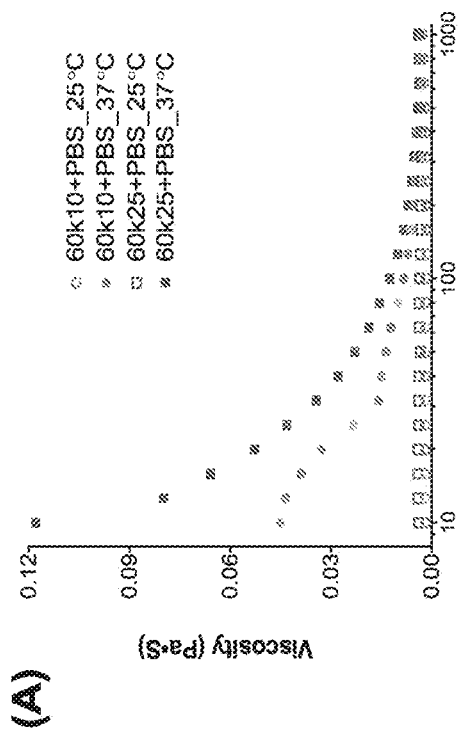
FIG. 5C is a plot of viscosity (Pa·s) versus temperature for an exemplary PNIPAM-MAA hydrogel at various shear stresses, according to one set of embodiments.
Figure 5D:
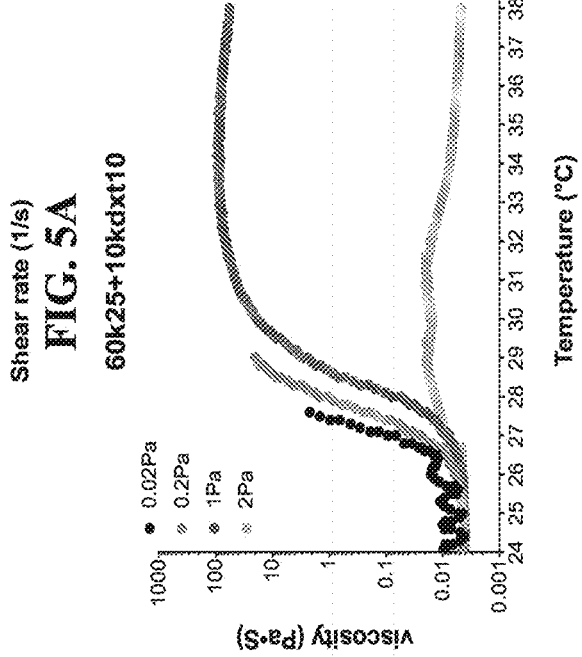
FIG. 5D is a plot viscosity (Pa·s) versus temperature for exemplary PNIPAM-MAA hydrogels with or without added dextran at various shear stresses, according to one set of embodiments.

FIGS. 5A-5D show the viscosity measurement of hydrogel formulations. (FIG. 5A) The viscosity of PNIPAM-MAA decreased as the shear rate increases at a temperature of 37° C., which indicates a shear-thinning behavior of the polymer after gelation. This is shear-thinning behavior is beneficial for reducing the possibility of forming obstruction in vivo after applying the polymer solution. The polymer at 25 mg/ml and 10 mg/ml both showed the shear-thinning behavior. (FIG. 5B) At a constant shear stress of 2 Pa, the viscosity was measured as a function of polymer at different concentrations. Note the dramatic change of viscosity from 0.01 to around 100 PaŸS after the gelation. (FIG. 5C) To evaluate the viscosity under different shear stress as a function of temperature, 60 k PNIPAM-MAA was used at 25 mg/ml with the addition of 10 k dextran at 10 mg/ml for the measurement. The reduced viscosity at 2 Pa than 1 Pa corresponds to the shear-thinning behavior that was shown in (FIG. 5A). (FIG. 5D) The effect of the addition of dextran on the viscosity of polymer solutions. For the 60 k PNIPAM-MAA solution used for the measurement, the 10 k dextran increases the viscosity higher than the addition of 70 k dextran to PNIPAM-MAA and PNIPAM-MAA in PBS. All viscosity measurements at 2 Pa were smaller than the viscosity at 1 Pa, which also corresponds with the shear-thinning behavior of the polymer solutions.

FIGS. 6A-6F show the synthesis and characterization of albumin nanoparticles (NPs). (FIG. 6A) Schematic of NP synthesis. HSA: human serum albumin. (FIG. 6B) Scanning Electron Microscopic (SEM) image of synthesized NPs. (FIGS. 6C-6E) Size, polydispersity index (PDI), and zeta potential measurement of synthesized NPs. 40, 80 and 120 indicate the concentration of HSA used for the NP synthesis. NP and HPNP denote uncoated and heparin coated NP, respectively. (F) Coating efficiency of heparin on the synthesized NPs. (FIGS. 6G and 6H) Budesonide and Granulocyte Macrophage-Co Stimulating Factor (GM-CSF) are used as model drugs loaded in HSA NPs, and the encapsulation efficiency and amount of each drug were quantified by HPLC or ELISA, respectively.

FIGS. 7A-7F show the evaluation of albumin nanoparticles in macrophage culture. Various synthesized HSA NPs were characterized and evaluated in macrophage culture. (FIG. 7A, 7B) Size, polydispersity index (PDI), and zeta potential measurement of uncoated and coated NPs in four formulations (1) NP: no drug unloaded; (2) B/NP: budesonide loaded; (3) G/NP: GM-CSF loaded NPs; (4) G+B/NP: budesonide and GM-CSF loaded NPs. (FIG. 7C) The inhibition effect of different NP formulations on TNF-α secretion in macrophage culture. Lipopolysaccharide (LPS) was used to activate the macrophages, which serve as a control. (FIG. 7D) The inhibition effect of different NP formulations on Nitric Oxide production in macrophage culture. LPS was used to activate the macrophages, which serve as a control. (FIG. 7E) The macrophage upake of HSA NPs at 4 h and 24 h after incubation was evaluated using fluorescence measurement by plate reader. (FIG. 7F) The macrophage upake of HSA NPs at 4 h and 24 h after incubation was evaluated using flow cytometry. The NPs showed a concentration-dependent uptake pattern by macrophages.

FIGS. 8A-8B show ex vivo retention of nanoparticles with mouse colon. (FIG. 8A) The HSA NPs with different size and zeta potential (G1, G2, G3, G4 and G5, see Table 1) were used to incubate with colons dissected from healthy mice (Healthy) or mice with colitis (DSS). The HSA NPs were labeled with an Alexa-Fluor640 dye for IVIS imaging. The fluorescence intensity of the colon after incubating with HSA NPs was quantified. G4 (250 nm, −36.4 mV) showed the significant higher retention in the colon with colitis than the healthy colon. (FIG. 8B) The retention of HSA NPs (G4) to mouse colon was also tested kinetically at different time points (10 min, 30 min, and 60 min) with healthy mice and mice with colitis. G4 showed significant higher retention to mouse colon with colitis than healthy colon at all time points tested. (n=5 mice in each group)

TABLE 1

|  | G1 | G2 | G3 | G4 | G5 |
| --- | --- | --- | --- | --- | --- |
| Average Cross-sectional Dimension (nm) | 120.48 | 185.7 | 209.6 | 242.5 | 202.733 |
| Average Zeta Potential (mV) | −37.8 | −48.2 | −46.4 | −36.4 | +4.01 |

FIGS. 9A-9B show in vivo retention of nanoparticles in mice. (FIG. 9A) Schematic of the experimental procedure. A single enema of dye-conjugated HSA NPs was given to mice with colitis or healthy mice. After 3 hours, mice were dissected and 3 cm of distal colon was taken for IVIS imaging. (FIG. 9B) IVIS quantification of budesonide-loaded HSA NPs evaluated in vivo after 3 hours of administration. The NPs showed significant higher retention in mouse colon with colitis than healthy colon (p=0.0283). (n=7 mice in each group)

Figures 10A, 10B:
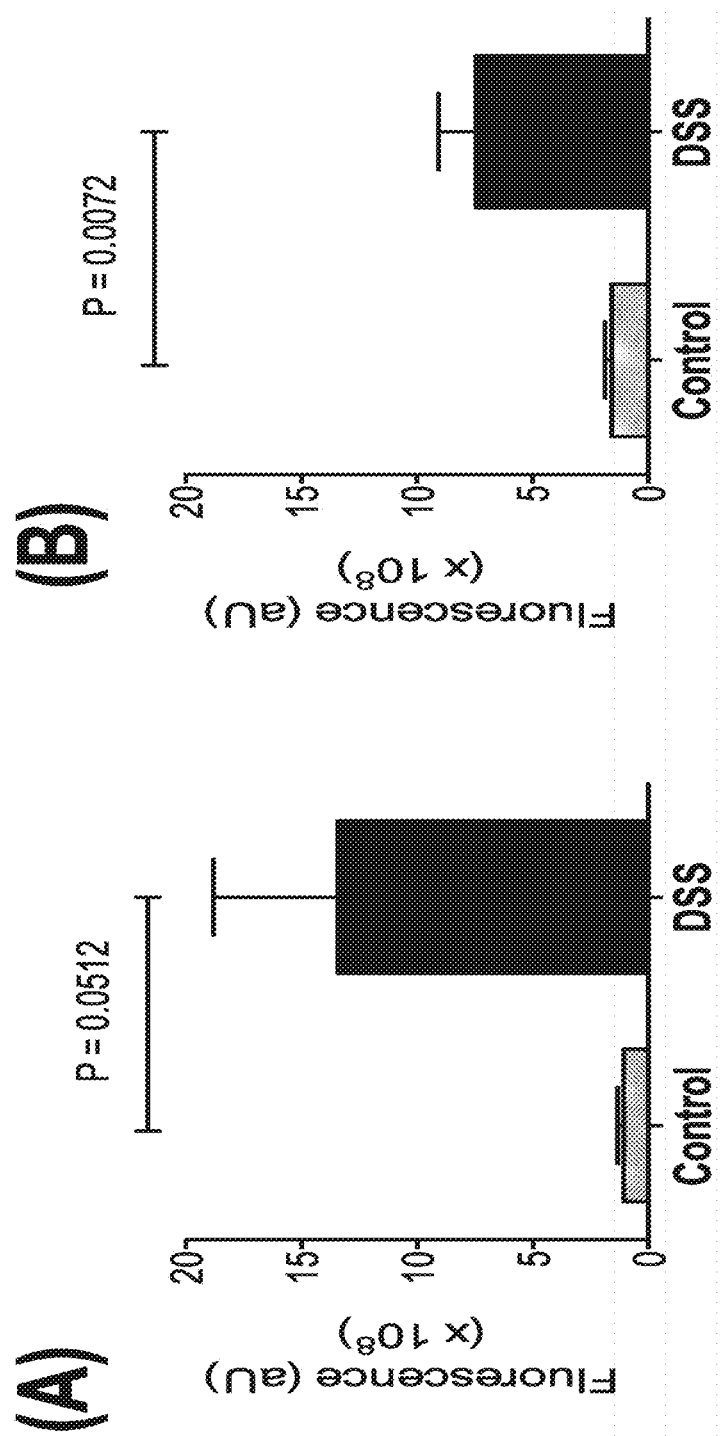
FIG. 10A is a plot of retention determined by fluorescence intensity for exemplary PNIPAM-MAA hydrogels comprising Texas-red labeled dextran (10 k) administered to colitic mice and control (healthy) mice, according to one set of embodiments.
FIG. 10B is a plot of retention determined by fluorescence intensity for control Texas-red labeled dextran (10 k) alone administered to colitic mice and control (healthy) mice, according to one set of embodiments.

FIGS. 10A-10B show in vivo retention of hydrogel formulations in mice. FIG. 10A shows IVIS quantification of the retention of modified PNIPAM-MAA with Texas-red labeled dextran (10 k) in colitic mice compared with healthy mice. The polymer and dye mixture showed much higher retention in colitis mice than healthy mice, which was evaluated 3 hours after the enema. (FIG. 10BB) The retention of Texas-red labeled dextran (10 k) alone was evaluated in vivo as a control. Although the dye alone also showed significant higher retention to colitic colon than healthy colon, the total retained fluorescence intensity was much higher in the polymer+dye mixture ($13.44 \times 10^8$) than the dye alone ($7.45 \times 10^8$).

Materials and Methods

Poly(N-isopropylacrylamide-co-methacrylic acid) (PNIPAM-COOH), succinic anhydride, Poly(N-isopropylacrylamide)-amine terminated, N-hydroxysulfosuccinimide (sulfo-NHS), dimethylamino pyridine, 2-aminoethane sulfonic acid (taurine), 1-ethyl-3-(3-dimethylamino-propyl carbodiimide) (EDC), 11-azido-3,6,9-trioxaundecan-1-amine, were purchased from Aldrich, acetylene-core bis-MPA dendron from Polymer Factory (Sweden, PFd-G2-Acetylene-OH), and used as received.

One-on-One Approach (Monofunctional)

PNIPAM-COOH was used as a starting material to couple taurine (S1) to PNIPAM-COOH backbone for enhanced negative charges that are not affected by pH in the environment. N,N-dimethylethylenediamine (N1) with positive charge was used as control.

Synthesis of PNIPAM-S1

PNIPAM-MAA (10 k and 60 k, respectively) with 10% MAA molar content was used for modification. The carboxylic acid on PNIPAM-MAA was functionalized with taurine (S1) or N, N-dimethyl-ethylenediamine (N1). Typically, 100 mg polymer was dissolved in distilled phosphate buffered saline (PBS, pH=7.4). Different amount of EDC and sulfo-NHS were added to the polymer solution to optimize the substitution efficiency. After synthesis, the resulting mixture was dialyzed against 0.2 M carbonate buffer (×6) and water (×3) (tubing with MWCO 3kDa) and then lyophilized. The structures of modified polymers were confirmed by H1-NMR.

Multiple-on-One Approach (Polyfunctional)

The "multiple-on-one" approach was used to synthesize dendrimers that contain multiple copies of taurine, and then conjugate the dendrimeric taurine to PNIAPM-COOH backbone via click chemistry to tune the charge densities on the PNIPAM-COOH.

Synthesis of Dendron-Acid 200 mg ($4.95 \times 10^{-4}$ moles) of 2,2-bismethylolpropionic acid (bis-MPA) generation 2 dendron with acetylene at the core, were dissolved in 1.5 mL of anhydrous pyridine in a Schlenck flask. To the stirring solution, 396 mg ($3.96 \times 10^{-3}$ moles) of succinic anhydride dissolved in 2.5 mL of anhydrous pyridine were added, and the mixture was left to stir at room temperature for 72 h. 10 mL of pentane were subsequently added, and the residue was washed with 3 mL of pentane twice. Residual paste was dissolved in 2 mL of THF, and precipitated by adding 6 mL of pentane. The recrystallization procedure was repeated 10 times, and the residue was dried in vacuum to yield a white solid.

Dendron Acid Functionalized with Taurine 30 mg (0.0373 mmol) were dissolved in 1:1 ratio mixture of 0.4 mL of dimethyl sulfoxide and 0.4 mL of dichloromethane, and placed in a Schlenck flask under nitrogen. To the stirring solution, 36.4 mg (0.315 mmol) of NHS dissolved in 1:1 ratio mixture of 0.2 mL of DMSO and 0.2 mL of DCM, and 11.5 mg (0.094 mmol) of DMAP dissolved in 1:1 ratio mixture of 0.25 mL of DMSO and 0.25 mL of DCM, 53 mg (0.341 mmol) of EDC dissolved in 1:1 ratio mixture of 0.4 mL of DMSO and 0.4 mL of DCM, were added in this sequence. The mixture was left to stir at room temperature for 24 h. Subsequently, 26.5 mg (0.212 mmol) of taurine, sonicated in 16 mL of DMSO for 30 minutes, and 19 mg (0.0262 mmol) of triethylamine, were added to the above mixture, and stirred under nitrogen for 48 h. Solvents were distilled off, and the mixture was dialyzed (MWCO 1 kDa, Regenerated Cellulose) against deionized water for 24 hours (×3 water exchange).

Reaction of Poly(NIPAM-Co-MAA) with 11-Azido-3,6,9-trioxaundecan-1-amine 201 mg (0.181 mmol) of Poly(NIPAM-Co-MAA) dissolved in 2.5 mL of DMSP were added to a Schlenck flask. To the stirring solution under nitrogen, 167.7 mg (1.457 mmol) of NHS dissolved in 1:1 ratio mixture of 0.8 mL of DMSO and 0.8 mL of dichloromethane, and 46 mg (0.376 mmol) of DMAP dissolved in 1:1 ratio mixture of 0.6 mL of DMSO and 0.6 mL of dichloromethane, and 117.6 mg (0.757 mmol) of EDC dissolved in 1:1 ratio mixture of 1 mL of DMSO and 1 mL of dichloromethane were added in this sequence. The reaction mixture was left to stir at room temperature under nitrogen for 48h. Subsequently 180 □L (0.825 mmol) of 11-azido-3,6,9-trioxaundecan-1-amine were added to the above solution mixture and left to stir at room temperature for 48 h. Solvent mixture was distilled off, and the resulting mixture was dialyzed against methanol for 24 hours (×3 methanol exchange). Methanol was subsequently removed to give a solid. The characteristic peak in the FT-IR at 2106 cm-1 for the terminal azide was clearly noted.

Reaction of Poly(N-isopropylacrylamide)-amine Terminated with Dendron Acid:

15.5 mg (0.0193 mmol) of dendron acid were dissolved in a 1:1 mixture of 1 mL of DMSO and 1 mL of dichloromethane and placed in a Schlenck flask under nitrogen. To the stirring solution 17 mg (0.148 mmol) of NHS dissolved in 1:1 mixture of 1 mL of DMSO and 1 mL of dichloromethane, followed by 8 mg (0.0655 mmol) of DMAP, and 24.7 mg (0.159 mmol) of EDC dissolved in a 1:1 mixture of 1 mL of DMSO and 1 mL of dichloromethane were added in this sequence. The clear solution was left to stir at room temperature for 48 h. 225.5 mg (0.1127 mmol) of amine terminated poly(NIPAM) dissolved in 5 mL of DMSO, followed by 0.014 mL of triethylamine were then added to the reaction mixture, and the solution mixture was left to stir at room temperature for 72 h. Solvent mixture was distilled off, and the resulting mixture was dialyzed against methanol for 24 hours (×3 methanol exchange). Methanol was subsequently removed to give a solid. The characteristic peak in the FT-IR at 2106 cm-1 for the terminal azide had decreased considerably in intensity.

Reaction of Poly(N-isopropylacrylamide)-amine Terminated with Dendron-Taurine 25 mg (0.0203 mmol) of dendron acid taurine were dissolved in 1:1 mixture of THF and Milli-Q water, and placed in a Schlenck flask under nitrogen. To the stirring solution 100 mg (0.01 mmol) of Poly-NIPAM-azide were added. It was followed by the addition of 10 mg of sodium ascorbate and 5 mg of copper sulphate dissolved in 0.5 mL of milli-Q water. The molar ratio of sodium ascorbate was 1:1 with the polymer, and that of CuSO4 was 1:0.5 with the polymer. The reaction was left to stir at room temperature overnight. Solvent mixture was distilled off, and the resulting mixture was dialyzed against methanol for 24 hours (×3 methanol exchange). Methanol was subsequently removed to give a light yellow solid. The characteristic peak in the FT-IR at 2106 cm-1 for the terminal azide had almost completely disappeared.

Lower Critical Solution Temperature (LCST) Determination

The modified polymers were dissolved in phosphate buffered saline (PBS, pH=7.4) for measurement of lower critical solution temperature (LCST) by UV-visible spectrophotometry (Cary 100 Bio UV-Vis) using quartz cuvette. The temperature ranged from 24° C. to 50° C. with a heat rate at 0.5° C./min.

Size and Zeta Potential Measurement

The size and surface charge of the polymeric hydrogels was determined at 37° C. using a Malvern Zetasizer (Nano-Series). The equilibrium time was 300 seconds before the measurement was perform for each temperature for the temperature testing range. Polymer solutions were diluted with 1 mM of NaCl to 0.05% for size and zeta measurement.

Viscosity Measurement

The viscosity measurement of polymer samples were measured using AR 2000 Rheometer connected with a Peltier plate for heat (TA Instruments Inc.) For the measurement of viscosity as a function of temperature, the temperature range is from 24° C. to 38° C., and the ramp rate is 0.50° C./min. The geometry used for the measurement is a 60 mm hard-anodized aluminum parallel plate, and the gap distance is 1000 μm.

Dual Loading of Budesonide and Granulocyte Macrophage Colony-Stimulating Factor (GM-CSF) into Heparin-Coated Human Serum Albumin Nanoparticles In a 20 mL-glass vial, 450 μL of 120 mg/mL HSA solution was mixed with 450 μL of 30.8 mg/mL GSH solution in water 22. The vial was placed in a 37° C. incubator and stirred for 1 hour at 800rpm. After 1 hour of incubation, 100 μL of GM-CSF solution (at various concentrations) was added to the glass vial at room temperature while stirring at 800 rpm. The mixture was stirred at room temperature for another 5 minutes. Then 4 mL of 3 mg/ml budesonide in 100% ethanol was added to the glass vial dropwise. The vial was placed back into the 37° C. incubator and stirred at 1100rpm for 10 minutes. The colloid was then placed in 100KDa dialysis tubing overnight at 4° C. After 24 hours, the colloid was taken out from the dialysis tubing, and an aliquot of 300 μL of HAS NPs was placed into a 1.5 mL microcentrifuge tube. 350 μL of 1 mg/mL heparin solution in water was added to the microcentrifuge tube dropwise. The tube was placed on a shake for 1 hour at room temperature with vigorous shaking. The colloid was then transferred to 100 kDa dialysis tubing and dialyzed against water for another 48 hours at room temperature. After dialysis, the size and zeta potential of the dual-loaded heparin-coated HSA NPs were measured. The encapsulated amount of budesonide and GM-CSF was quantified by high performance liquid chromatography (HPLC) and ELISA, respectively.

In Vivo Adhesion Assay of Functionalized Polymers

Adult BALB/c WT mice were purchased from the Jackson Laboratory. All mouse studies were performed according to institutional and NIH guidelines for humane animal use. Experimental protocols were approved by the Animal Care Committees at the Massachusetts Institute of Technology. Animals with colitis (DSS) and disease-free controls (untreated WT) were on an Alfalfa-free diet (Harlan Laboratories) for one week before experiments. For in vivo adhesion testing, animals were fasted overnight, and the following morning, each mouse received an enema of 100 μl of polymer solution containing the polymer and Texas-red labeled dextran. Individual mice were anesthetized with 2.5% isoflurane, a 20-G flexible disposable feeding needle (Braintree Scientific) was advanced into the rectum 3 cm past the anus, the polymer solution was administered, the catheter was removed and the anus was kept closed manually for 1 minute. Animals were sacrificed after 3 hours. The distal 3 cm of the colon were removed and imaged freshly without washing. The fluorescence signal intensity was quantified using Living Image software (version 4.3.1, Perkin Elmer) in a standard-size region of interest (ROI) drawn around individual colon pieces. Background fluorescence intensity determined as the average of three ROIs not containing any colon tissue was subtracted from all specimens.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

The invention claimed is:

1. An article, comprising:
a solution comprising a plurality of nanoparticles and a thermoresponsive polymer comprising one or more ligands attached to the polymer, wherein:
the solution is configured to undergo a sol-to-gel transition between ambient conditions and physiological conditions, the sol-to-gel transition comprises a phase transition from a liquid phase to a solid or semi-solid phase;
the plurality of nanoparticles comprises a therapeutic agent; and
the one or more ligands comprise a negatively charged functional group under physiological conditions, and wherein the thermoresponsive polymer has a structure as in:

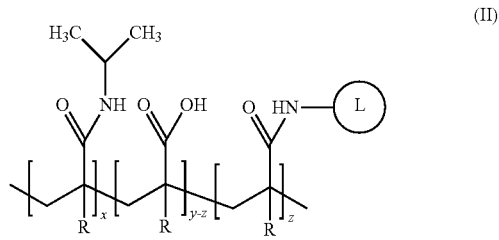

(II)

wherein:
x is 0.01-1,
y is 1-x,
z is 0.01-1,
L is a ligand, and
each R is the same or different and is hydrogen or alkyl.

2. An article as in claim 1, wherein the plurality of nanoparticles are configured to have a size and/or charge that facilitate adhesion to an inflamed tissue at a location internal a subject.

3. An article as in claim 1, wherein the ligand is configured to adhere to inflamed mucosa but not healthy mucosa.

4. An article as in claim 1, wherein the ligand comprises a functional group comprising sulfonic acid, sulfinic acid, phosphonic acid, phsophinic acid, derivatives thereof, esters thereof, or salts thereof.

5. An article as in claim 1, wherein the ligand is selected from the group consisting of taurine, 2-aminoethyl hydrogen sulfate, O-phosphorylethanolamine, and 2-aminoethylphosphonic acid.

6. An article as in claim 1, wherein the thermoresponsive polymer comprises a first monomer selected from the group consisting of N-isopropyl acrylamide (NIPAM), N-isopropyl methacrylamide (NIPMAM), N,N-diethyl-acrylamide (DEAAAM), N-vinylcaprolactam (VCL), and 3-(N,N-dimethylamino) propylmethacrylamide (DMAPMA).

7. An article as in claim 6, wherein the thermoresponsive polymer comprises a monomer selected from the group consisting of acrylic acid (AA) or methacrylic acid (MAA).

8. An article as in claim 1, wherein the sol-to-gel transition occurs at a temperature in the range of 32° C. to 42° C.

9. An article as in claim 1, wherein the thermoresponsive polymer comprises a dendritic ligand.

10. An article as in claim 1, wherein the therapeutic agent is configured to be released from the thermoresponsive polymer via diffusion and/or stimuli-triggered release such that the therapeutic agent exhibits a zero-order or first-order release profile.

11. An article as in claim 1, wherein the thermoresponsive polymer has a number average molecular weight greater than or equal to 1 kDa and less than or equal to 200 kDa.

12. An article as in claim 1, wherein the thermoresponsive polymer is retained at a location internal to a subject for greater than or equal to 10 min.

13. An article as in claim 1, wherein the nanoparticle comprises a matrix comprising albumin.

14. An article as in claim 1, wherein the nanoparticle comprises a coating comprising heparin.

15. An article as in claim 1, wherein the thermoresponsive polymer has a lower critical solution temperature, wherein the thermoresponsive polymer is a liquid phase at a temperature below the lower critical solution temperature and is a solid or semi-solid phase at a temperature above the lower critical solution temperature.

16. An article, comprising:
a thermoresponsive polymer comprising a polymer backbone, wherein the thermoresponsive polymer is configured to undergo sol-to-gel phase transition from a liquid phase at ambient conditions to a solid or semi-solid phase at physiological conditions;
a plurality of nanoparticles associated with the polymer, the plurality of nanoparticles comprising one or more therapeutic agents; and
a ligand attached to the polymer comprising a negatively charged functional group under physiological conditions,
wherein the thermoresponsive polymer has a structure as in:

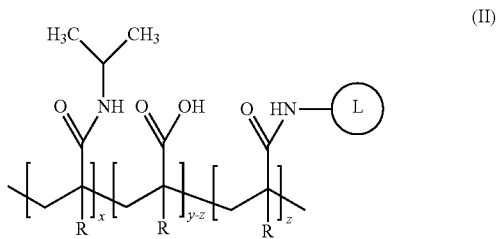

wherein:
x is 0.01-1,
y is 1-x,
z is 0.01-1,
L is a ligand, and
each R is the same or different and is hydrogen or alkyl.

17. An article, comprising
a plurality of nanoparticles comprising a shell and/or a matrix;
a coating disposed on a surface of the nanoparticle; and
a therapeutic agent encapsulated or embedded within the nanoparticle,
wherein the shell and/or the matrix comprises albumin and wherein the coating comprises heparin; and a thermoresponsive polymer having a structure as in:

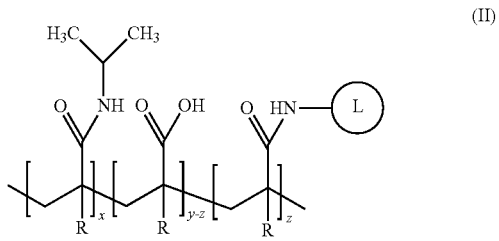

wherein:
x is 0.01-1,
y is 1-x,
z is 0.01-1,
L is a ligand, and
each R is the same or different and is hydrogen or alkyl.

* * * * *